US005777097A

United States Patent [19]
Lee et al.

[11] Patent Number: 5,777,097
[45] Date of Patent: Jul. 7, 1998

[54] OLIGONUCLEOTIDES COMPRISING A REGION OF A CYTOKINE SUPPRESSIVE ANTI-INFLAMMATORY DRUG BINDING PROTEIN

[75] Inventors: John C. Lee, Berwyn; Jerry L. Adams, Wayne; Timothy F. Gallagher, Harleysville; David W. Green, Bryn Mawr; John Richard Heys, Malvern; Peter C. McDonnell, Elkins Park; Dean E. McNulty, Philadelphia, all of Pa.; Peter R. Young, Lawrenceville, N.J.; James E. Strickler, Milton, Mass.

[73] Assignee: SmithKline Beecham Corporation, Philadelphia, Pa.

[21] Appl. No.: 469,421

[22] Filed: Jun. 6, 1995

Related U.S. Application Data

[63] Continuation-in-part of Ser. No. 250,975, May 31, 1994, which is a continuation-in-part of Ser. No. 123,175, Sep. 17, 1993, abandoned.

[51] Int. Cl.[6] .................................................. C07H 21/04
[52] U.S. Cl. .................................. 536/24.31; 536/24.3
[58] Field of Search ........................... 536/23.5, 23.1, 536/24.3, 24.31; 435/320.1, 69.1, 172.3, 240.1, 252.3

[56] References Cited

U.S. PATENT DOCUMENTS

| 4,778,806 | 10/1988 | Bender et al. | 514/336 |
| 4,780,470 | 10/1988 | Bender et al. | 514/341 |
| 4,794,114 | 12/1988 | Bender et al. | 514/224.2 |
| 5,317,019 | 5/1994 | Bender et al. | 514/224.2 |

OTHER PUBLICATIONS

Lee et al. 1989. Agents and Actions 27:277–9.
Lee et al. 1990. Int. J. Immunother. 6:1–12.
Griswold et al. 1993. Drugs Exptl. Clin. Res. 19:243–8.
Han et al. 1995. Biochimica et Biophysica Acta 1265: 224–227.
Rouse et al. 1994. Cell 78:1027–1037.

*Primary Examiner*—Elizabeth C. Kemmerer
*Attorney, Agent, or Firm*—William T. King; Edward T. Lentz

[57] ABSTRACT

This invention relates to drug binding proteins, to genes encoding same and to assays and methods for screening pharmaceuticals. More specifically, this invention relates to a Cytokine Suppressive Anti-Inflammatory Drug (CSAID) binding protein, to a gene encoding same and to assays and screens useful in the evaluation and characterization of drugs of this pharmacologic class.

1 Claim, 26 Drawing Sheets

Kd=3.641E-9 M Bmax=5.205E-12 M values are IC50, μM

| COMPOUND | R1/R2 | X-Y | IL-1 | TNF | THP-1 cytosol binding |
|---|---|---|---|---|---|
| XI(a) | 4-pyridyl / 4-FPh | -CH$_2$CH$_2$S- | 0.5 | 0.4 | <0.1 |
| XI(b) | 4-FPh / 4-pyridyl | -CH$_2$CH$_2$S- | >5 | >5 | 10 |
| XI(c) | 4-pyridyl / 4-FPh | -CH$_2$CH$_2$CH$_2$- | 0.2 | 0.2 | <0.1 |
| XI(d) | 4-FPh / 4-pyridyl | -CH$_2$CH$_2$CH$_2$- | <5 | <5 | <10 |
| XI(e) | 4-pyridyl / 4-MeSPh | -CH$_2$CH$_2$CH$_2$- | 2.7 | 2.7 | 3.4 |
| XI(i) | 4-MeSPh / 4-pyridyl | -CH$_2$CH$_2$CH$_2$- | >5 | >5 | 5 |
| XI(g) | 4-pyridyl / 4-FPh | -CH$_2$CH$_2$OAc,H | 0.5 | 3 | 0.5 |
| XI(h) | 4-FPh / 4-pyridyl | -CH$_2$CH$_2$OAc,H | 5 | 5 | >10 |

1    AACATTGTGAAATGTCAGAAGCTTACAGATGACCATGTTCAGTTCCTTATCTACCAAATT
     AsnIleValLysCysGlnLysLeuThrAspAspHisValGlnPheLeuIleTyrGlnIle    60

61   CTCCGAGGTCTAAAGTATATACATTCAGCTGACATAATTCACAGGGACCTAAAACCTAGT
     LeuArgGlyLeuLysTyrIleHisSerAlaAspIleIleHisArgAspLeuLysProSer   120

121  AATCTAGCTGTGAATGAAGACTGTGAGCTGGAAGATTCTGGATTTTGGACTTGGCTCGGCAC
     AsnLeuAlaValAsnGluAspCysGluLeuLysIleLeuAspPheGlyLeuAlaArgHis   180

181  ACAGATGATGAAATGACAGGCTACGTGGCCACTAGGTGGTATGCTACTAGGTGGTATGCTACAGGGATCATG
     ThrAspAspGluMetThrGlyTyrValAlaThrArgTrpTyrArgAlaProGluIleMet   240

241  CTGAACTGGATGCATTACAACCAGACAGgTGGTATTTGGGTCAAG    285
     LeuAsnTrpMetHisTyrAsnGlnThrGlyGlyIleTrpValLys

FIG. 13

CAAGTCCcAATCCTCCCCAACCACAGCAAGTTGAATTTATCAACCATGTTGGGTTGTAAA

TGCTCGTGTGATTTCCTACAAGAAATACCTGCTCTGAATATTTTTGTAATAAAGGTCTTT

GCACATGTGACCCACAATACGTGTTAGGAGCCTGCATGCTCTGGAAGCCTGGACTCTAAG

CTGGAGCTCTTGGAAGAGCTCTTCGGTTTCTGAGCATAATGCTCCCATCTCCTGATTTCT

CTGAACAGAAAaCaAAAGAGAGAATGAGGGAAATTGCTATTTTATTTGTATTCATGAACT

TGGCTGTAATCAGTTATGCCGTATAGGAtGTCAGACAATACCACTGGTTAAAATAAAGCC

TATTTTTCAAATTTAAAAAAAAAAAAAAAAAA

FIG. 14

```
..355nts..GCCGCTGGAAAATGTCTCAGGAGAGGCCCACGTTCTACCGGCAGGAGCTGAACAAGACAATCTGG  420
              M  S  Q  E  R  P  T  F  Y  R  Q  E  L  N  K  T  I  W          18

GAGGTGCCCGAGCGTTACCAGAACCTGTCTCCAGTGGGCTCTGGCGCCTATGGCTCTGTGTGTGCTGCTTTTGAC  495
 E  V  P  E  R  Y  Q  N  L  S  P  V  G  S  G  A  Y  G  S  V  C  A  A  F  D   43

ACAAAAACGGGGTTACGTGTGGCAGTGAAGAAGCTCTCCAGACCATTTCAGTCCATCATTCATGCGAAAAGAACC  570
 T  K  T  G  L  R  V  A  V  K  K  L  S  R  P  F  Q  S  I  I  H  A  K  R  T   68

TACAGAGAACTGCGGTTACTTAAACATATGAAACATGAAAATGTGATTGGTCTGTTGGACGTTTTTACACCTGCA  645
 Y  R  E  L  R  L  L  K  H  M  K  H  E  N  V  I  G  L  L  D  V  F  T  P  A   93

AGGTCTCTGGAGGAATTCAATGATGTGTATCTGGTGACCCATCTCATGGGGGCAGATCTGAACAACATTGTGAAA  720
 R  S  L  E  E  F  N  D  V  Y  L  V  T  H  L  M  G  A  D  L  N  N  I  V  K   118

TGTCAGAAGCTTACAGATGACCATGTTCAGTTCCTTATCTACCAAATTCTCCGAGGTCTAAAGTATATACATTCA  795
 C  Q  K  L  T  D  D  H  V  Q  F  L  I  Y  Q  I  L  R  G  L  K  Y  I  H  S   143

GCTGACATAATTCACAGGGACCTAAAACCTAGTAATCTAGCTGTGAATGAAGACTGTGAGCTGAAGATTCTGGAT  870
 A  D  I  I  H  R  D  L  K  P  S  N  L  A  V  N  E  D  C  E  L  K  I  L  D   168

TTTGGACTGGCTCGGCACACAGATGATGAAATGACAGGCTACGTGGCCACTAGGTGGTACAGGGCTCCTGAGATC  945
 F  G  L  A  R  H  T  D  D  E  M  T  G  Y  V  A  T  R  W  Y  R  A  P  E  I   193

ATGCTGAACTGGATGCATTACAACCAGACAGTTGATATTTGGTCAGTGGGATGCATAATGGCCGAGCTGTTGACT  1020
 M  L  N  W  M  H  Y  N  Q  T  V  D  I  W  S  V  G  C  I  M  A  E  L  L  T   218

GGAAGAACATTGTTTCCTGGTACAGACCATATTAACCAGCTTCAGCAGATTATGCGTCTGACAGGAACACCCCCC  1095
 G  R  T  L  F  P  G  T  D  H  I  N  Q  L  Q  Q  I  M  R  L  T  G  T  P  P   243

GCTTATCTCATTAACAGGATGCCAAGCCATGAGGCAAGAAACTATATTCAGTCTTTGACTCAGATGCCGAAGATG  1170
 A  Y  L  I  N  R  M  P  S  H  E  A  R  N  Y  I  Q  S  L  T  Q  M  P  K  M   268

AACTTTGCGAATGTATTTATTGGTGCCAATCCCCTGGCTGTCGACTTGCTGGAGAAGATGCTTGTATTGGACTCA  1245
 N  F  A  N  V  F  I  G  A  N  P  L  A  V  D  L  L  E  K  M  L  V  L  D  S   293

GATAAGAGAATTACAGCGGCCCAAGCCCTTGCACATGCCTACTTTGCTCAGTACCACGATCCTGATGATGAACCA  1320
 D  K  R  I  T  A  A  Q  A  L  A  H  A  Y  F  A  Q  Y  H  D  P  D  D  E  P   318

GTGGCCGATCCTTATGATCAGTCCTTTGAAAGCAGGGACCTCCTTATAGATGAGTGGAAAAGCCTGACCTATGAT  1395
 V  A  D  P  Y  D  Q  S  F  E  S  R  D  L  L  I  D  E  W  K  S  L  T  Y  D   343

GAAGTCATCAGCTTTGTGCCACCACCCCTTGACCAAGAAGAGATGGAGTCCTGAGCACCT...2330nts..
 E  V  I  S  F  V  P  P  P  L  D  Q  E  E  M  E  S  *
```

FIG. 16

```
                                    110                        297
                              GADLNNIVKCQKLTD           ITAAQALAHAYFAQY 1                                                                                  360
        ┌──────────────────────────────────────────────────────────────────────────────────┐
        │                        CSAIDS BINDING PROTEIN (CSBP)                              │
        └──────────────────────────────────────────────────────────────────────────────────┘
```

1054  AACCAGCTTCAGCAGATTATGCGTCTGACACAGGAACACCCCCGCTTATCTCATTAACAGGATGCCAAGCCATGAG  1128
 230    N  Q  L  Q  Q  I  M  R  L  T  G  T  P  P  A  Y  L  I  N  R  M  P  S  H  E   255

230    D  Q  L  K  L  I  L  R  L  V  G  T  P  G  A  E  L  L  K  K  I  S  S  E  S   255
1054  GATCAGTTGAAGCTCATTTTAAGACTCGTTGGAACCCCAGGGGCTGAGCTTTTGAAGAAAATCTCCTCAGAGTCT  1128

FIG. 17

```
                    1                                                                          50
Human Erk1     MAAAAAQGGG  GGEPRRTEGV  GPGVPGEVEM  VKGQ....PF  DVGPRYTQLQ
Human Erk2     MAAAAAAGAG  P.........  ........EM  VRGQ....VF  DVGPRYTNLS
        Csbp   ..........  ..........  ..MSQERPTF  YRQELNKTIW  EVPERYQNLS
   Yeast Hog1  ..........  ..........  ...MTTNEEF  IRTQIFGTVF  EITNRYNDLN
       Identity ..........  ..........  ..........  ..........  ....RY..L.

51    I                       II                      III      100
Human Erk1     YIGEGAYGMV  SSAYDHVRKT  RVAIKKIS.P  FEHQTYCQRT  LREIQILLRF
Human Erk2     YIGEGAYGMV  CSAYDNVNKV  RVAIKKIS.P  FEHQTYCQRT  LREIKILLRF
        Csbp   PVGSGAYGSV  CAAFDTKTGL  RVAVKKLSRP  FQSIIHAKRT  YRELRLLKHM
   Yeast Hog1  PVGMGAFGLV  CSATDTLTSQ  PVAIKKIMKP  FSTAVLAKRT  YRELKLLKHL
       Identity ..G.GA.G.V  ...A.D....  .VA.KK...P  F.......RT  .RE...L...

101  IV                       V                                150
Human Erk1     RHENVIGIRD  IL.RASTLEA  MRDVYIVQDL  METDLYKLLK  SQQLSNDHIC
Human Erk2     RHENIIGIND  II.RAPTIEQ  MKDVYIVQDL  METDLYKLLK  TQHLSNDHIC
        Csbp   KHENVIGLLD  VFTPARSLEE  FNDVYLVTHL  MGADLNNIVK  CQKLTDDHVQ
   Yeast Hog1  RHENLICLQD  IF.....LSP  LEDIYFVTEL  QGTDLHRLLQ  TRPLEKQFVQ
       Identity .HEN.I...D  ..........  ..D.Y.V..L  ...DL.....  ...L......

151  VI                                            VII  200
Human Erk1     YFLYQILRGL  KYIHSANVLH  RDLKPSNLLI  NTTCDLKICD  FGLARIADPE
Human Erk2     YFLYQILRGL  KYIHSANVLH  RDLKPSNLLL  NTTCDLKICD  FGLARVADPD
        Csbp   FLIYQILRGL  KYIHSADIIH  RDLKPSNLAV  NEDCELKILD  FGLARHTDDE
   Yeast Hog1  YFLYQILRGL  KYVHSAGVIH  RDLKPSNILI  NENCDLKICD  FGLARIQDPQ
       Identity ...YQILRGL  KY.HSA...H  RDLKPSN...  N..C.LKI.D  FGLAR..D..

201   * *   VIII                       IX              250
Human Erk1     HDHTGFLTEY  VATRWYRAPE  IMLNSKGYTK  SIDIWSVGCI  LAEMLSNRPI
Human Erk2     HDHTGFLTEY  VATRWYRAPE  IMLNSKGYTK  SIDIWSVGCI  LAEMLSNRPI
        Csbp   ......MTGY  VATRWYRAPE  IMLNWMHYNQ  TVDIWSVGCI  MAELLTGRTL
   Yeast Hog1  ......MTGY  VSTRYYRAPE  IMLTWQKYDV  EVDIWSAGCI  FAEMIEGKPL
       Identity .......T.Y  V.TR.YRAPE  IML....Y..  ..DIWS.GCI  .AE.......

251                     X                              300
Human Erk1     FPGKHYLDQL  NHILGILGSP  SQEDLNCIIN  MKARNYLQSL  PSKTKVAWAK
Human Erk2     FPGKHYLDQL  NHILGILGSP  SQEDLNCIIN  LKARNYLLSL  PHKNKVPWNR
        Csbp   FPGTDHINQL  QQIMRLTGTP  PAYLINRMPS  HEARNYIQSL  TQMPKMNFAN
        Csbp2  -------DQL  KLILRLVGTP  GAELLKKISS  ES--------  ----------
   Yeast Hog1  FPGKDHVHQF  SIITDLLGSP  PKDVINTICS  ENTLKFVTSL  PHRDPIPFSE
       Identity FPG.....Q.  ..I....G.P  ..........  ........SL  ..........

301                  XI                                350
Human Erk1     LFPKSDSKAL  DLLDRMLTFN  PNKRITVEEA  LAHPYLEQYY  DPTDEPVAEE
Human Erk2     LFPNADSKAL  DLLDKMLTFN  PHKRIEVEQA  LAHPYLEQYY  DPSDEPIAEA
        Csbp   VFIGANPLAV  DLLEKMLVLD  SDKRITAAQA  LAHAYFAQYH  DPDDEPVADP
   Yeast Hog1  REKTVEPDAV  DLLEKMLVFD  PKKRITAADA  LAHPYSAPYH  DPTDEPVADA
       Identity .F......A.  DLL..ML...  ..KRI....A  LAH.Y...Y.  DP.DEP.A..

351                                                    400
Human Erk1     PFTFAMELDD  LPKERLKELI  FQETARFQPG  VLEAP.....  ..........
Human Erk2     PFKFDMELDD  LPKEKLKELI  FEETARFQPG  YRS.......  ..........
        Csbp   .YDQSFESRD  LLIDEWKSLT  YDEVISFVPP  PLDQEEMES.  ..........
   Yeast Hog1  KFDWHFNDAD  LPVDTWRVMM  YSEILDFHKI  GGSDGQIDIS  ATFDDQVAAA
       Identity ..........D  L.........  ..E....F..  ..........  ..........
```

FIG. 19

```
  1   GGAACCCGCGACCACTGGGAGCCTTAGGGGGGCCAGCAGCTGGAACGGAGTACTGCGACGCAGCCCGAGTCGGCC

76   TTGTAGGGGCGAAGTGTCAGGGAGATCGCGGGGCGCAGTCTTGAGCGCGGAGCGCGTCCCTGCCCTTAGCGG

151   GGCTTGCCCCAGTCGCAGGGGCACATCCGCGCGCCTGCGCTGACAGCAGCGCGGAGCGCGGGAGTCTGCGGGTC

226   GCGGCAGCCGCACCTGCGCGGGGCGACCAGCAAGGTCCCCCCGGTCGGGGGCAGCAAGGGCCGGGGAGAG

301   GGTGCGGGTGCAGGGGCCCCACAGGGCCCACCTTCTGCCCGGCGGCCCGCTGCCCGCTGAAATGTCTCAGGAGA
 -19                                                                   MetSerGlnGluA

376   GGCCCACGTTCTACCGGCAGGAGCTGAACAAGACAATCTGGAGTGCCCAGAGCTTACCAGACCTGTCTCCAG
  6   rgProThrPheTyrArgGlnGluLeuAsnLysThrIleTrpGluValProGluArgTyrGlnAsnLeuSerProV

451   TGGGCTCTGCGCCTATGCCTCTGTCTGTGTGTTTGACAAAACGGGTAGTGTGGCAGTGAAGAAGC
 31   alGlySerGlyAlaTyrGlySerValCysAlaAlaPheAspThrLysThrGlyLeuArgValAlaValLysL

526   TCTCCAGACCATTCAGTCCATCATTCATGCGAAAAGAACCTACAGAGAACTGCGGTTACTTAAACATATGAAAC
 56   euSerArgProPheGlnSerIleIleHisAlaLysArgThrTyrArgGluLeuArgLeuLeuLysHisMetLys

601   ATGAAAATGTGATTGGTATGGCTCTGGAGATCTCTGAGAATTCAATGATGTGTATCTGG
 81   isGluAsnValIleGlyLeuLeuAspLeuLeuAspSerLeuGluGluPheAsnAspValTyrLeuV

676   TGACCACATCTCATGGGGGCAGATCGAACAACATTGTGAAATGTCAGAAGCTTACAGATGACCATGTTCAGTTCC
106   alThrHisLeuMetGlyAlaAspLeuAsnAsnIleValLysCysGlnLysLeuThrAspAspHisValGlnPheL

751   TTATCTACCAAATTCTCCGAGGTCTAAAGTATATACATTCAGTGACATAATTCACAGGACCTAAAACCTAGTA
131   euIleTyrGlnIleLeuArgGlyLeuLysTyrIleHisSerAlaAspIleIleHisArgAspLeuLysProSerA
```

FIG. 21A

```
 826  ATCTAGCTGTGAATGAAGACTGTGAGCTGATTTTGACTGCTCGGCACACAGATGATGAAATGA
 156  snLeuAlaValAspCysGluLeuLysIleLeuAspPheGlyLeuAlaArgHisThrAspGluMetT

901  CAGGCTACGTGGCCACTAGGTGGTACAGGGCTCCTGAGATCATGCTGAACTGCATTACAACCAGACAGTTG
 181  hrGlyTyrValAlaThrArgTrpTyrArgAlaProGluIleMetLeuAsnTrpMetHisTyrAsnThrValA

976  ATATTGGTCAGTGGGATGCATAATGGCCGAGCTGTTGACTGGAAGAACATTGTTCCTGGTACAGACCATATTA
 206  spIleTrpSerValGlyCysIleMetAlaGluLeuLeuThrGlyArgThrLeuPheProGlyThrAspHisIleA

1051  AccagcttcagcagaATTAtgctgtcgacaggaacACCCCcgcttatctcattaacaggatgccaagccatgagG
 231  snGlnLeuGlnIleMetArgLeuThrGlyThrProProAlaTyrLeuIleAsnArgMetProSerHisGluA 1126  CAAGAAACTATATTCAGTCTTTGCTGAAGATGCCGAAGATGAACTTTGCGAATGTATTATTGGTCCAATCCC
 256  laArgAsnTyrIleGlnSerLeuLeuLysMetProLysMetProLysMetProLysMetAsnValPheIleGlyAlaAsnProL 1201  TGGCTGTCGACTTGCTGGAGAAGATGCTTGTATTGGACTCAGATAAGAGATCAGATGAGGACCCAAGCCTTGCAC
 281  euAlaValAspLeuLeuGluLysMetLeuValLeuAspSerAspLysArgIleThrAlaAlaGlnAlaLeuAlaH 1276  ATGCCTACTTTGCTCAGTACCACGATCCTGATGATGAACCAGTGCCGATCCTTATGATCAGTCCTTTGAAAGCA
 306  isAlaTyrPheAlaGlnTyrHisAspProAspAspGluProValAlaAspProTyrAspGlnSerPheGluSerA 1351  GGGACCTCCTTATAGATGAGTGGAAAAGCCTGACTAGTGAAGTCATCAGTTTGTCCACCCCCTGACC
 331  rgAspLeuLeuIleAspGluTrpLysSerLeuThrSerGluValIleSerPheValProProLeuAspG 1426  AAGAAGAGATGGAGTCCTGAGCACCCTGGTTCTCTTCTCTGTGATCCCCACTTCACTGTGAGGGGAAGGCCTTTCA
 356  lnGluMetGluSerEnd 1501  CGGGAACTCTCCAAATATTATTCAAGTGCCTCTTGTTGCAGAGATTCCTCCATGTGGAAGGGGTGCCGTGC
```

```
1576  GTGTGCGTGCGTGTTAGTGTGTGTGTGCATGTGTCTTTGTGGAGGTAAGACAATATGAACAAACTAT
1651  GATCACAGTGACTTTACACGAGGTTGTGGATGCTCCACCTTGCTCTTTCTGAGAGTTGGC
1726  TCAGGCAGACAAGAGCTGCTGCTCCTTTAGGAATATGTTCAATGCAAAGTAAAAAATATGAATTGTCCCCAATC

1801  CCGGTCATGCTCTTTGCCACTTGGCTTCTCCCTGTGACCCCACCTTCTGTTGCTTCTGTGTTCAGACCTGCTTCAGACCTGATACGTACCAGC
1876  ACAGTGGCACGGAGAGAAGGCCCATACCTTCTGTTGCTTCAGACCTGATACGTACACTGATACGTACAGC
1951  CAAAAAGGACCAACTGGCTTCTGTGCACTAGCCTGTGATTAACTGCTTAGTATGTTCTCAGATCTTGACAGTA
2026  TATTTGAAACTGTAAATATGTTTGTGCCTTAAAAGGAGAAGAAAGTGTAGATAGTTAAAGACTGCAGCTGCT
2101  GAAGTTCTGAGCCCGGGCAAGTCGAGAGGGCTGTTGGACCCGGAGTAATCAGGCAGCCTTCA
2176  TAGGCGGTCATGTGCATGTGAGCACATGCGTATATGCGTATCCCCAGTAGTCAGAAGCAGTTCTG
2251  TTTCTCTGCTTACCCTTCACCTTTGGCTGTACTCTTTATTTCTAGCAGAGTGAGGATGTGTTTTGCACGTCTTGCTATTGAGCA
2326  ATGTCATGTACTTCCTGTACTCTTTATTTCTAGCAGAGTGAGGATGTGTTTTGCACGTCTTGCTATTGAGCA
2401  TGCACAGCTTGCTGTCCTGCTCTTGCTCTTCAGGAGGCCCTGGTGTCAGGCAGTTGCCAGTGAAGACTTCTGGTA
2476  GTTTAGATCCACATGTCACCTCAGCTGATATATGGCAAGTGATATACCTTCTTCAGCCCCTAGTGCTATTCTG
```

FIG. 21D

```
2551  TGTGAACACAATTGATACTTCAGTGCTTTGATGTGAAATCATGAAAAGAGAACAGGTGGATGTATAGCAT
2626  TTTTATTCATGCCATCTGTTTTCAACCAACTATTTTGAGGAATTATCATGGGAAAAGACCAGGGCTTTCCCAG
2701  GAATATCCCAAACTTCGGAAACAAGTTATTCTTCACTCCCAATAACTAATGCTAAGAAATGCTGAAAATCAAA
2776  GTAAAAAATTAAGCCCATAAGGCCAGAAACTCCTTTGCTGTCTTTCTCTAAATATGATTACTTTAAAATAAAA
2851  AAGTAACAAGTGTCTTTTCCACTCCTATGGAAAAGGGTCTCTGGCAGCTAACATGACTTCTTGCTTTGGG
2926  GAGAAATAAATTTGTTTCAGAATTTGTATAGGAATCCCTTTGAGAATGTGATCCTTTGATGGGAG
3001  AAAGGGCAAATTATTTTAATATTTTGTATTTCAACTTTATAAAGATAAATATCCTCAGGGCTGAGAAGTGTC
3076  GTTTTCATAACTGCTGAATTTCAGGCATTTGTTCTACATGAGGACTCATATATTTAAGCCTTTGTGTAATAA
3151  GAAAGTATAAGTCACTTCCAGTGTGTGGCGTGTGACAGAATCTGTATTGGGCCAAGGTGTTCCATTTCTCA
3226  ATCAGTGCAGTGATACATGTACTCCAGAGGACGGGGTGGACCCCCCTGAGTCAACTGAGCAAGAAGGAGG
3301  CAGACTGATGGCGATTCCCCTCTCACCCGGGACTCCCCTTTCAAGAAAGTGAACCTTTAAAGTAAAGGCCTC
3376  ATCCCTTTATGCAGTTCAAATCCTCACCATCCACAGCAAGATGAATTTTATCAGCCATGTTTGGTTGTAAATG
```

```
3451  CTCGTGTGATTCCTACAGAAATACTGCTCTGAATATTTGTAATAAAGGTCTTTGCACATGTGACCACATACGT
3526  GTTAGGAGGCTGCATGCTCTGGAAGCCTGACTCTAAGCCTGGAGCTCTTCGTTTCTGAGCAT
3601  AATGCTCCCATCTCCTGATTTCTCTGAACAGAAAACAAAGAGAGAATGAGGGAAATGCTATTTTATTTGTATT
3676  CATGAACTTGGCTGTAATCAGTTATGCCGTATAGGATGTCAGACAATACCACTGGTTAAAATAAAGCCTATTTTT
3751  CAAATTTAAAAAAAAAAAAAAAA  3775
```

FIG. 21E

```
  1   CGCCCCAGTGCCAGGGCCACATCCAGCCCGCTGGGCTGACAGCAGCCCGGCCCGGGAGTCTGCGGGTCGCG

76   CAGCCGCCACCTGCGGGCGACCAGCGGCAAGGTCCCCGGCCTGGGCGGGGCAGCAAGGCCCGGGAGAGGGTG

151   CGGGTGCAGGCGGCCCCACAGGGCCACCTTCTGCCCGGCCGCTGAAAATGTCTCAGGAGAGCC
-18                                                    MetSerGlnGluArgPr

226   CACGTTCTACCGGCAGGAGCTGAACAAGACAATCTGGGAGGTGCCCGAGGGTTACCAGAACCTGTCTCCAGTGG
  7   oThrPheTyrArgGlnGluLeuAsnLysThrIleTrpGluValProGluGlyTyrGlnAsnLeuSerProValGl

301   CTCTGGCGCCTATGCTCTCTGCTCTGTCTGTCTTTGCACACAAAAACGGGTTACGGTGTGCCAGTGAAGAAGCTCTC
 32   ySerGlyAlaTyrGlyLeuSerValCysAlaAlaPheAspThrLysThrGlyLeuArgValAlaValLysLysLeuSe

376   CAGACCATTTCAGTCCATCATTCATGCGAAAAGAACCTACAGAGAACTGCGTTACTTAAACATATGAAACATGA
 57   rArgProPheGlnSerIleIleHisAlaLysArgThrTyrArgGluLeuLeuLysHisMetLysHisGl

451   AAATGTGATTGGTCTCTGTGACGTTTTTACACCTGCAAGGCTCTGGAGGAATTCAATGATGTATCTGTGAC
 82   uAsnValIleGlyLeuCysAspValPheThrProAlaArgSerLeuGluGluPheAsnAspValTyrLeuValTh

526   CCATCTCATGGGGCAGATCTGAACAACATGTGAAATGTCAGAAGCTTACAGATGCTAAAAGCTTACGATGTTCAGTCCTTAT
107   rHisLeuMetGlyAlaAspLeuAsnAsnIleValLysCysGlnLysLeuThrAspAspHisValGlnPheLeuIl

601   CTACCAAATTCTCCGAGGTCTAAAGTATATACATTCAGTGCTAAATCAGCTGACACATAATTCACAGGACCTAAAACCTAGTAATCT
132   eTyrGlnIleLeuArgGlyLeuLysTyrIleHisSerAlaAlaAspIleIleHisArgAspLeuLysProSerAsnLe

676   AGCTGTGAATGAAGACTGTGAGCTGAAGATTCTGGATTTTGGACTGGCTCGCCACACAGATGATGAAATGACAGG
157   uAlaValAsnGluAspCysGluLeuLysIleLeuAspPheGlyLeuAlaArgHisThrAspAspGluMetThrGl

751   CTACGTGGCCACTAGGTGGTACAGGGCTCCTGAGATCATGCTGAACTGAGATCATTACAACCAGACAGTTGATAT
182   yTyrValAlaThrArgTrpTyrArgAlaProGluIleMetLeuAsnTrpMetHisTyrAsnGlnThrValAspIl
```

FIG. 22A

```
826   TTGGTCAGTGGGATGCATAATGCCGAGCTGTTGACTGGAAGAACATTGTTCCTGTGTACAGAGACCATATTGATCA
207         eTrpSerValGlyCysIleMetAlaGluLeuLeuThrGlyArgThrLeuPheProGlyThrAspHisIleAspGl

901   GTTGAAGCTCATTTAAGACTCGTTGGAACTCCAGGGGCTGAGCTTTTGAAGAAATCTCTCAGAGTCTGCAAG
232         nLeuLysLeuIleLeuArgLeuValGlyThrProGlyAlaGluLeuLeuLysLysIleSerSerGluSerAlaAr

976   AAACTATATTCAGTCTTTGACTCAGAGATGCCGAAGATGAACTTTGCGAATGTATTTATTGGTGCCAATCCCCTGGC
257         gAsnTyrIleGlnSerLeuThrGlnMetProLysMetAsnPheAlaAsnValPheIleGlyAlaAsnProLeuAl

1051  TGTCGACTTGCTCGAGAAGATGCTTGTATTGGACTCAGATAAGAGAATTACAGCGGCCCAAGCCCTTGCACATGC
282         aValAspLeuLeuGluLysMetLeuValLeuAspSerAspLysArgIleThrAlaAlaGlnAlaLeuAlaHisAl

1126  CTACTTTGCTCAGTACCACGATCCTGATGAACCAGTGCCCATCCTTATGATCCTTGAAAGCAGGA
307         aTyrPheAlaGlnTyrHisAspProAspGluProValAlaAlaAspProTyrAspGlnSerPheGluSerArgAs

1201  CCTCCTTATAGAGTGGAAAAGCCTGACCTATGAAGTCATCAGCTTTGTGCCACCCCTTGACCAAGA
332         pLeuLeuIleAspGluTrpLysSerLeuThrTyrTyrAspGluValIleSerPheValProProLeuAspGlnGl

1276  AGAGATGGAGTCCTGAGCACCTGGTTCTCTGTTCTGATCCATGTGAGGGAAGGCCTTTTCACGGG
357         uGluMetGluSerEnd

1351  AACTCTCCAAATATTATTCAAGTGCCAAAAA  1381
```

FIG.22B

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens
        ( G ) CELL TYPE: Monocyte
        ( H ) CELL LINE: THP.1

( x i ) SEQUENCE DESCRIPTION: SEQ ID NO:1:

```
Ile  Thr  Ala  Ala  Gln  Ala  Leu  Ala  His  Ala  Tyr  Phe  Ala  Gln  Tyr
 1                  5                       10                      15
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: HOMO SAPIENS
        ( G ) CELL TYPE: MONOCYTE
        ( H ) CELL LINE: THP.1

( x i ) SEQUENCE DESCRIPTION: SEQ ID NO:2:

```
Xaa  Gln  Leu  Leu  Asn  Asn  Ile  Val  Lys  Phe  Gln  Lys  Leu  Thr
 1                  5                       10
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
        ( A ) ORGANISM: HOMO SAPIENS
        ( G ) CELL TYPE: MONOCYTE ( x i ) SEQUENCE DESCRIPTION: SEQ ID NO:3:

GCYCAYGCTA YTTYGCYCAR TA 22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
        ( A ) ORGANISM: HOMO SAPIENS
        ( G ) CELL TYPE: MONOCYTE ( x i ) SEQUENCE DESCRIPTION: SEQ ID NO:4:

AAYAAYATYK TBAARTTYCA AA 22

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: HOMO SAPIENS
        ( G ) CELL TYPE: MONOCYTE
        ( H ) CELL LINE: THP.1

( x i ) SEQUENCE DESCRIPTION: SEQ ID NO:5:

Asn Ile Val Lys Cys Gln Lys Leu Thr
 1               5

( 2 ) INFORMATION FOR SEQ ID NO:6:

( i ) SEQUENCE CHARACTERISTICS:
        ( A ) LENGTH: 285 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS
        ( G ) CELL TYPE: MONOCYTE
        ( H ) CELL LINE: THP.1

( i x ) FEATURE:
        ( A ) NAME/KEY: CDS
        ( B ) LOCATION: 1..285

( x i ) SEQUENCE DESCRIPTION: SEQ ID NO:6:

| | | | | | | | | | | | | | | | | |
|---|---|---|---|---|---|---|---|---|---|---|---|---|---|---|---|---|
| AAC | ATT | GTG | AAA | TGT | CAG | AAG | CTT | ACA | GAT | GAC | CAT | GTT | CAG | TTC | CTT | 48 |
| Asn | Ile | Val | Lys | Cys | Gln | Lys | Leu | Thr | Asp | Asp | His | Val | Gln | Phe | Leu | |
| 1 | | | | 5 | | | | | 10 | | | | | 15 | | |
| ATC | TAC | CAA | ATT | CTC | CGA | GGT | CTA | AAG | TAT | ATA | CAT | TCA | GCT | GAC | ATA | 96 |
| Ile | Tyr | Gln | Ile | Leu | Arg | Gly | Leu | Lys | Tyr | Ile | His | Ser | Ala | Asp | Ile | |
| | | | 20 | | | | | 25 | | | | | 30 | | | |
| ATT | CAC | AGG | GAC | CTA | AAA | CCT | AGT | AAT | CTA | GCT | GTG | AAT | GAA | GAC | TGT | 144 |
| Ile | His | Arg | Asp | Leu | Lys | Pro | Ser | Asn | Leu | Ala | Val | Asn | Glu | Asp | Cys | |
| | | 35 | | | | | 40 | | | | | 45 | | | | |
| GAG | CTG | AAG | ATT | CTG | GAT | TTT | GGA | CTG | GCT | CGG | CAC | ACA | GAT | GAT | GAA | 192 |
| Glu | Leu | Lys | Ile | Leu | Asp | Phe | Gly | Leu | Ala | Arg | His | Thr | Asp | Asp | Glu | |
| | 50 | | | | | 55 | | | | | 60 | | | | | |
| ATG | ACA | GGC | TAC | GTG | GCC | ACT | AGG | TGG | TAC | AGG | GCT | CCT | GAG | ATC | ATG | 240 |
| Met | Thr | Gly | Tyr | Val | Ala | Thr | Arg | Trp | Tyr | Arg | Ala | Pro | Glu | Ile | Met | |
| 65 | | | | | 70 | | | | | 75 | | | | | 80 | |
| CTG | AAC | TGG | ATG | CAT | TAC | AAC | CAG | ACA | GGT | GGT | ATT | TGG | GTC | AAG | | 285 |
| Leu | Asn | Trp | Met | His | Tyr | Asn | Gln | Thr | Gly | Gly | Ile | Trp | Val | Lys | | |
| | | | | 85 | | | | | 90 | | | | | 95 | | |

( 2 ) INFORMATION FOR SEQ ID NO:7:

( i ) SEQUENCE CHARACTERISTICS:
        ( A ) LENGTH: 95 amino acids
        ( B ) TYPE: amino acid
        ( D ) TOPOLOGY: linear ( ii ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Asn | Ile | Val | Lys | Cys | Gln | Lys | Leu | Thr | Asp | Asp | His | Val | Gln | Phe | Leu |
| 1 | | | | 5 | | | | | 10 | | | | | 15 | |
| Ile | Tyr | Gln | Ile | Leu | Arg | Gly | Leu | Lys | Tyr | Ile | His | Ser | Ala | Asp | Ile |
| | | | 20 | | | | | 25 | | | | | 30 | | |
| Ile | His | Arg | Asp | Leu | Lys | Pro | Ser | Asn | Leu | Ala | Val | Asn | Glu | Asp | Cys |
| | | 35 | | | | | 40 | | | | | 45 | | | |
| Glu | Leu | Lys | Ile | Leu | Asp | Phe | Gly | Leu | Ala | Arg | His | Thr | Asp | Asp | Glu |
| | 50 | | | | | 55 | | | | | 60 | | | | |
| Met | Thr | Gly | Tyr | Val | Ala | Thr | Arg | Trp | Tyr | Arg | Ala | Pro | Glu | Ile | Met |
| 65 | | | | | 70 | | | | | 75 | | | | | 80 |
| Leu | Asn | Trp | Met | His | Tyr | Asn | Gln | Thr | Gly | Gly | Ile | Trp | Val | Lys | |
| | | | | 85 | | | | | 90 | | | | | 95 | |

( 2 ) INFORMATION FOR SEQ ID NO:8:

( i ) SEQUENCE CHARACTERISTICS:
        ( A ) LENGTH: 392 base pairs
        ( B ) TYPE: nucleic acid
        ( C ) STRANDEDNESS: single
        ( D ) TOPOLOGY: linear ( ii ) MOLECULE TYPE: cDNA ( iii ) HYPOTHETICAL: NO ( iv ) ANTI-SENSE: NO ( vi ) ORIGINAL SOURCE:
        ( A ) ORGANISM: HOMO SAPIENS
        ( G ) CELL TYPE: MONOCYTE
        ( H ) CELL LINE: THP.1

( ix ) FEATURE:
        ( A ) NAME/KEY: 3'UTR
        ( B ) LOCATION: 1..392

( x i ) SEQUENCE DESCRIPTION: SEQ ID NO:8:

-continued

| | | | | | |
|---|---|---|---|---|---|
| CAAGTCCCAA | TCCTCCCCAA | CCACAGCAAG | TTGAATTTAT | CAACCATGTT | GGGTTGTAAA | 60 |
| TGCTCGTGTG | ATTTCCTACA | AGAAATACCT | GCTCTGAATA | TTTTTGTAAT | AAAGGTCTTT | 120 |
| GCACATGTGA | CCCACAATAC | GTGTTAGGAG | CCTGCATGCT | CTGGAAGCCT | GGACTCTAAG | 180 |
| CTGGAGCTCT | TGGAAGAGCT | CTTCGGTTTC | TGAGCATAAT | GCTCCCATCT | CCTGATTTCT | 240 |
| CTGAACAGAA | AACAAAGAG | AGAATGAGGG | AAATTGCTAT | TTTATTTGTA | TTGATGAACT | 300 |
| TGGCTGTAAT | CAGTTATGCC | GTATAGGATG | TCAGACAATA | CCACTGGTTA | AAATAAAGCC | 360 |
| TATTTTTCAA | ATTTAAAAAA | AAAAAAAAAA | AA | | | 392 |

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (xi) SEQUENCE DESCRIPTION: SEQ ID NO:9:

| | | |
|---|---|---|
| CCTCGGAGAA | TTTGGTAGAT | AAGG | 24 |

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (xi) SEQUENCE DESCRIPTION: SEQ ID NO:10:

| | | | |
|---|---|---|---|
| AACATTGTGA | AATGTCAGAA | GCTTACAGAT | GACCAT | 36 |

(2) INFORMATION FOR SEQ ID NO:11:

(i) SEQUENCE CHARACTERISTICS:
        (A) LENGTH: 3813 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (ix) FEATURE:

( A ) NAME/KEY: CDS
( B ) LOCATION: 379..1461

( x i ) SEQUENCE DESCRIPTION: SEQ ID NO:11:

```
CCTCCTGGTA  TAATCTGGAA  CCGCGACCAC  TGGAGCCTTA  GCGGGCGCAG  CAGCTGGAAC   60

GGGAGTACTG  CGACGCAGCC  CGGAGTCGGC  CTTGTAGGGG  CGAAGGTGCA  GGGAGATCGC  120

GGCGGGCGCA  GTCTTGAGCG  CCGGAGCGCG  TCCCTGCCCT  TAGCGGGGCT  TGCCCCAGTC  180

GCAGGGGCAC  ATCCAGCCGC  TGCGGCTGAC  AGCAGCCGCG  CGCGCGGGAG  TCTGCGGGGT  240

CGCGGCAGCC  GCACCTGCGC  GGGCGACCAG  CGCAAGGTCC  CCGCCCGGCT  GGGCGGGCAG  300

CAAGGGCCGG  GGAGAGGGTG  CGGGTGCAGG  CGGGGGCCCC  ACAGGGCCAC  CTTCTTGCCC  360

GGCGGCTGCC  GCTGGAAA ATG TCT CAG GAG AGG CCC ACG TTC TAC CGG CAG        411
                     Met Ser Gln Glu Arg Pro Thr Phe Tyr Arg Gln
                      1               5                      10
```

| | | | | | | | | | | | | | | | | |
|---|---|---|---|---|---|---|---|---|---|---|---|---|---|---|---|---|
| GAG | CTG | AAC | AAG | ACA | ATC | TGG | GAG | GTG | CCC | GAG | CGT | TAC | CAG | AAC | CTG | 459 |
| Glu | Leu | Asn | Lys | Thr | Ile | Trp | Glu | Val | Pro | Glu | Arg | Tyr | Gln | Asn | Leu | |
| | | | 15 | | | | | 20 | | | | | 25 | | | |
| TCT | CCA | GTG | GGC | TCT | GGC | GCC | TAT | GGC | TCT | GTG | TGT | GCT | GCT | TTT | GAC | 507 |
| Ser | Pro | Val | Gly | Ser | Gly | Ala | Tyr | Gly | Ser | Val | Cys | Ala | Ala | Phe | Asp | |
| | | 30 | | | | | 35 | | | | | 40 | | | | |
| ACA | AAA | ACG | GGG | TTA | CGT | GTG | GCA | GTG | AAG | AAG | CTC | TCC | AGA | CCA | TTT | 555 |
| Thr | Lys | Thr | Gly | Leu | Arg | Val | Ala | Val | Lys | Lys | Leu | Ser | Arg | Pro | Phe | |
| | 45 | | | | | 50 | | | | | 55 | | | | | |
| CAG | TCC | ATC | ATT | CAT | GCG | AAA | AGA | ACC | TAC | AGA | GAA | CTG | CGG | TTA | CTT | 603 |
| Gln | Ser | Ile | Ile | His | Ala | Lys | Arg | Thr | Tyr | Arg | Glu | Leu | Arg | Leu | Leu | |
| 60 | | | | | 65 | | | | | 70 | | | | | 75 | |
| AAA | CAT | ATG | AAA | CAT | GAA | AAT | GTG | ATT | GGT | CTG | TTG | GAC | GTT | TTT | ACA | 651 |
| Lys | His | Met | Lys | His | Glu | Asn | Val | Ile | Gly | Leu | Leu | Asp | Val | Phe | Thr | |
| | | | | 80 | | | | | 85 | | | | | 90 | | |
| CCT | GCA | AGG | TCT | CTG | GAG | GAA | TTC | AAT | GAT | GTG | TAT | CTG | GTG | ACC | CAT | 699 |
| Pro | Ala | Arg | Ser | Leu | Glu | Glu | Phe | Asn | Asp | Val | Tyr | Leu | Val | Thr | His | |
| | | | 95 | | | | | 100 | | | | | 105 | | | |
| CTC | ATG | GGG | GCA | GAT | CTG | AAC | AAC | ATT | GTG | AAA | TGT | CAG | AAG | CTT | ACA | 747 |
| Leu | Met | Gly | Ala | Asp | Leu | Asn | Asn | Ile | Val | Lys | Cys | Gln | Lys | Leu | Thr | |
| | | 110 | | | | | 115 | | | | | 120 | | | | |
| GAT | GAC | CAT | GTT | CAG | TTC | CTT | ATC | TAC | CAA | ATT | CTC | CGA | GGT | CTA | AAG | 795 |
| Asp | Asp | His | Val | Gln | Phe | Leu | Ile | Tyr | Gln | Ile | Leu | Arg | Gly | Leu | Lys | |
| | 125 | | | | | 130 | | | | | 135 | | | | | |
| TAT | ATA | CAT | TCA | GCT | GAC | ATA | ATT | CAC | AGG | GAC | CTA | AAA | CCT | AGT | AAT | 843 |
| Tyr | Ile | His | Ser | Ala | Asp | Ile | Ile | His | Arg | Asp | Leu | Lys | Pro | Ser | Asn | |
| 140 | | | | | 145 | | | | | 150 | | | | | 155 | |
| CTA | GCT | GTG | AAT | GAA | GAC | TGT | GAG | CTG | AAG | ATT | CTG | GAT | TTT | GGA | CTG | 891 |
| Leu | Ala | Val | Asn | Glu | Asp | Cys | Glu | Leu | Lys | Ile | Leu | Asp | Phe | Gly | Leu | |
| | | | | 160 | | | | | 165 | | | | | 170 | | |
| GCT | CGG | CAC | ACA | GAT | GAT | GAA | ATG | ACA | GGC | TAC | GTG | GCC | ACT | AGG | TGG | 939 |
| Ala | Arg | His | Thr | Asp | Asp | Glu | Met | Thr | Gly | Tyr | Val | Ala | Thr | Arg | Trp | |
| | | | 175 | | | | | 180 | | | | | 185 | | | |
| TAC | AGG | GCT | CCT | GAG | ATC | ATG | CTG | AAC | TGG | ATG | CAT | TAC | AAC | CAG | ACA | 987 |
| Tyr | Arg | Ala | Pro | Glu | Ile | Met | Leu | Asn | Trp | Met | His | Tyr | Asn | Gln | Thr | |
| | | 190 | | | | | 195 | | | | | 200 | | | | |
| GTT | GAT | ATT | TGG | TCA | GTG | GGA | TGC | ATA | ATG | GCC | GAG | CTG | TTG | ACT | GGA | 1035 |
| Val | Asp | Ile | Trp | Ser | Val | Gly | Cys | Ile | Met | Ala | Glu | Leu | Leu | Thr | Gly | |
| | 205 | | | | | 210 | | | | | 215 | | | | | |
| AGA | ACA | TTG | TTT | CCT | GGT | ACA | GAC | CAT | ATT | AAC | CAG | CTT | CAG | CAG | ATT | 1083 |
| Arg | Thr | Leu | Phe | Pro | Gly | Thr | Asp | His | Ile | Asn | Gln | Leu | Gln | Gln | Ile | |
| 220 | | | | | 225 | | | | | 230 | | | | | 235 | |
| ATG | CGT | CTG | ACA | GGA | ACA | CCC | CCC | GCT | TAT | CTC | ATT | AAC | AGG | ATG | CCA | 1131 |
| Met | Arg | Leu | Thr | Gly | Thr | Pro | Pro | Ala | Tyr | Leu | Ile | Asn | Arg | Met | Pro | |
| | | | | 240 | | | | | 245 | | | | | 250 | | |

| | | | | | | | | | | | | | | | | |
|---|---|---|---|---|---|---|---|---|---|---|---|---|---|---|---|---|
| AGC | CAT | GAG | GCA | AGA | AAC | TAT | ATT | CAG | TCT | TTG | ACT | CAG | ATG | CCG | AAG | 1179 |
| Ser | His | Glu | Ala | Arg | Asn | Tyr | Ile | Gln | Ser | Leu | Thr | Gln | Met | Pro | Lys | |
| | | | 255 | | | | | 260 | | | | | 265 | | | |
| ATG | AAC | TTT | GCG | AAT | GTA | TTT | ATT | GGT | GCC | AAT | CCC | CTG | GCT | GTC | GAC | 1227 |
| Met | Asn | Phe | Ala | Asn | Val | Phe | Ile | Gly | Ala | Asn | Pro | Leu | Ala | Val | Asp | |
| | | 270 | | | | | 275 | | | | | 280 | | | | |
| TTG | CTG | GAG | AAG | ATG | CTT | GTA | TTG | GAC | TCA | GAT | AAG | AGA | ATT | ACA | GCG | 1275 |
| Leu | Leu | Glu | Lys | Met | Leu | Val | Leu | Asp | Ser | Asp | Lys | Arg | Ile | Thr | Ala | |
| | 285 | | | | | 290 | | | | | 295 | | | | | |
| GCC | CAA | GCC | CTT | GCA | CAT | GCC | TAC | TTT | GCT | CAG | TAC | CAC | GAT | CCT | GAT | 1323 |
| Ala | Gln | Ala | Leu | Ala | His | Ala | Tyr | Phe | Ala | Gln | Tyr | His | Asp | Pro | Asp | |
| 300 | | | | | 305 | | | | | 310 | | | | | 315 | |
| GAT | GAA | CCA | GTG | GCC | GAT | CCT | TAT | GAT | CAG | TCC | TTT | GAA | AGC | AGG | GAC | 1371 |
| Asp | Glu | Pro | Val | Ala | Asp | Pro | Tyr | Asp | Gln | Ser | Phe | Glu | Ser | Arg | Asp | |
| | | | | 320 | | | | | 325 | | | | | 330 | | |
| CTC | CTT | ATA | GAT | GAG | TGG | AAA | AGC | CTG | ACC | TAT | GAT | GAA | GTC | ATC | AGC | 1419 |
| Leu | Leu | Ile | Asp | Glu | Trp | Lys | Ser | Leu | Thr | Tyr | Asp | Glu | Val | Ile | Ser | |
| | | | 335 | | | | | 340 | | | | | 345 | | | |
| TTT | GTG | CCA | CCA | CCC | CTT | GAC | CAA | GAA | GAG | ATG | GAG | TCC | TGAGCACCTG | | | 1468 |
| Phe | Val | Pro | Pro | Pro | Leu | Asp | Gln | Glu | Glu | Met | Glu | Ser | | | | |
| | | 350 | | | | | 355 | | | | | 360 | | | | |

| | | | | |
|---|---|---|---|---|
| GTTTCTGTTC | TGTTGATCCC | ACTTCACTGT | GAGGGGAAGG | CCTTTTCACG | GGAACTCTCC | 1528 |
| AAATATTATT | CAAGTGCCTC | TTGTTGCAGA | GATTTCCTCC | ATGGTGGAAG | GGGGTGTGCG | 1588 |
| TGCGTGTGCG | TGCGTGTTAG | TGTGTGTGCA | TGTGTGTGTC | TGTCTTTGTG | GGAGGGTAAG | 1648 |
| ACAATATGAA | CAAACTATGA | TCACAGTGAC | TTTACAGGAG | GTTGTGGATG | CTCCAGGGCA | 1708 |
| GCCTCCACCT | TGCTCTTCTT | TCTGAGAGTT | GGCTCAGGCA | GACAAGAGCT | GCTGTCCTTT | 1768 |
| TAGGAATATG | TTCAATGCAA | AGTAAAAAAA | TATGAATTGT | CCCCAATCCC | GGTCATGCTT | 1828 |
| TTGCCACTTT | GGCTTCTCCT | GTGACCCCAC | CTTGACGGTG | GGGCGTAGAC | TTGACAACAT | 1888 |
| CCCACAGTGG | CACGGAGAGA | AGGCCCATAC | CTTCTGGTTG | CTTCAGACCT | GACACCGTCC | 1948 |
| CTCAGTGATA | CGTACAGCCA | AAAAGGACCA | ACTGGCTTCT | GTGCACTAGC | CTGTGATTAA | 2008 |
| CTTGCTTAGT | ATGGTTCTCA | GATCTTGACA | GTATATTTGA | AACTGTAAAT | ATGTTTGTGC | 2068 |
| CTTAAAAGGA | GAGAAGAAAG | TGTAGATAGT | TAAAAGACTG | CAGCTGCTGA | AGTTCTGAGC | 2128 |
| CGGGCAAGTC | GAGAGGGCTG | TTGGACAGCT | GCTTGTGGGC | CCGGAGTAAT | CAGGCAGCCT | 2188 |
| TCATAGGCGG | TCATGTGTGC | ATGTGAGCAC | ATGCGTATAT | GTGCGTCTCT | CTTTCTCCCT | 2248 |
| CACCCCCAGG | TGTTGCCATT | TCTCTGCTTA | CCCTTCACCT | TGGTGCAGA | GGTTCTTGA | 2308 |
| ATATCTGCCC | CAGTAGTCAG | AAGCAGGTTC | TTGATGTCAT | GTACTTCCTG | TGTACTCTTT | 2368 |
| ATTTCTAGCA | GAGTGAGGAT | GTGTTTTGCA | CGTCTTGCTA | TTTGAGCATG | CACAGCTGCT | 2428 |
| TGTCCTGCTC | TCTTCAGGAG | GCCCTGGTGT | CAGGCAGGTT | TGCCAGTGAA | GACTTCTTGG | 2488 |
| GTAGTTAGA | TCCCATGTCA | CCTCAGCTGA | TATTATGGCA | AGTGATATCA | CCTCTCTTCA | 2548 |
| GCCCCTAGTG | CTATTCTGTG | TTGAACACAA | TTGATACTTC | AGGTGCTTTT | GATGTGAAAA | 2608 |
| TCATGAAAAG | AGGAACAGGT | GGATGTATAG | CATTTTTATT | CATGCCATCT | GTTTCAACC | 2668 |
| AACTATTTTT | GAGGAATTAT | CATGGGAAAA | GACCAGGGCT | TTCCCAGGA | ATATCCCAAA | 2728 |
| CTTCGGAAAC | AAGTTATTCT | CTTCACTCCC | AATAACTAAT | GCTAAGAAAT | GCTGAAAATC | 2788 |
| AAAGTAAAAA | ATTAAAGCCC | ATAAGGCCAG | AAACTCCTTT | TGCTGTCTTT | CTCTAAATAT | 2848 |
| GATTACTTTA | AAATAAAAAA | GTAACAAGGT | GTCTTTTCCA | CTCCTATGGA | AAAGGGTCTT | 2908 |
| CTTGGCAGCT | TAACATTGAC | TTCTTGGTTT | GGGGAGAAAT | AAATTTTGTT | TCAGAATTTT | 2968 |
| GTATATTGTA | GGAATCCCTT | TGAGAATGTG | ATTCCTTTTG | ATGGGGAGAA | AGGGCAAATT | 3028 |

-continued

```
ATTTTAATAT  TTTGTATTTT  CAACTTTATA  AAGATAAAAT  ATCCTCAGGG  GTGGAGAAGT    3088
GTCGTTTTCA  TAACTTGCTG  AATTTCAGGC  ATTTTGTTCT  ACATGAGGAC  TCATATATTT    3148
AAGCCTTTTG  TGTAATAAGA  AAGTATAAAG  TCACTTCCAG  TGTTGGCTGT  GTGACAGAAT    3208
CTTGTATTTG  GGCCAAGGTG  TTTCCATTTC  TCAATCAGTG  CAGTGATACA  TGTACTCCAG    3268
AGGGACGGGT  GGACCCCCTG  AGTCAACTGG  AGCAAGAAGG  AAGGAGGCAG  ACTGATGGCG    3328
ATTCCCTCTC  ACCCGGGACT  CTCCCCCTTT  CAAGGAAAGT  GAACCTTTAA  AGTAAAGGCC    3388
TCATCTCCTT  TATTGCAGTT  CAAATCCTCA  CCATCCACAG  CAAGATGAAT  TTTATCAGCC    3448
ATGTTTGGTT  GTAAATGCTC  GTGTGATTTC  CTACAGAAAT  ACTGCTCTGA  ATATTTTGTA    3508
ATAAAGGTCT  TTGCACATGT  GACCACATAC  GTGTTAGGAG  GCTGCATGCT  CTGGAAGCCT    3568
GGACTCTAAG  CTGGAGCTCT  TGGAAGAGCT  CTTCGGTTTC  TGAGCATAAT  GCTCCCATCT    3628
CCTGATTTCT  CTGAACAGAA  AACAAAGAG   AGAATGAGGG  AAATTGCTAT  TTTATTTGTA    3688
TTCATGAACT  TGGCTGTAAT  CAGTTATGCC  GTATAGGATG  TCAGACAATA  CCACTGGTTA    3748
AAATAAAGCC  TATTTTTCAA  ATTTAAAAAA  AAAAAAAAA   AAGTCCAGCA  ATTTCGTTAC    3808
TTATG                                                                    3813
```

(2) INFORMATION FOR SEQ ID NO:12:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:12:

```
Met  Ser  Gln  Glu  Arg  Pro  Thr  Phe  Tyr  Arg  Gln  Glu  Leu  Asn  Lys  Thr
  1                   5                        10                       15

Ile  Trp  Glu  Val  Pro  Glu  Arg  Tyr  Gln  Asn  Leu  Ser  Pro  Val  Gly  Ser
              20                       25                       30

Gly  Ala  Tyr  Gly  Ser  Val  Cys  Ala  Ala  Phe  Asp  Thr  Lys  Thr  Gly  Leu
         35                       40                       45

Arg  Val  Ala  Val  Lys  Lys  Leu  Ser  Arg  Pro  Phe  Gln  Ser  Ile  Ile  His
    50                       55                       60

Ala  Lys  Arg  Thr  Tyr  Arg  Glu  Leu  Arg  Leu  Leu  Lys  His  Met  Lys  His
 65                       70                       75                       80

Glu  Asn  Val  Ile  Gly  Leu  Leu  Asp  Val  Phe  Thr  Pro  Ala  Arg  Ser  Leu
                   85                       90                       95

Glu  Glu  Phe  Asn  Asp  Val  Tyr  Leu  Val  Thr  His  Leu  Met  Gly  Ala  Asp
              100                      105                      110

Leu  Asn  Asn  Ile  Val  Lys  Cys  Gln  Lys  Leu  Thr  Asp  Asp  His  Val  Gln
             115                      120                      125

Phe  Leu  Ile  Tyr  Gln  Ile  Leu  Arg  Gly  Leu  Lys  Tyr  Ile  His  Ser  Ala
    130                      135                      140

Asp  Ile  Ile  His  Arg  Asp  Leu  Lys  Pro  Ser  Asn  Leu  Ala  Val  Asn  Glu
145                      150                      155                      160

Asp  Cys  Glu  Leu  Lys  Ile  Leu  Asp  Phe  Gly  Leu  Ala  Arg  His  Thr  Asp
             165                      170                      175

Asp  Glu  Met  Thr  Gly  Tyr  Val  Ala  Thr  Arg  Trp  Tyr  Arg  Ala  Pro  Glu
             180                      185                      190

Ile  Met  Leu  Asn  Trp  Met  His  Tyr  Asn  Gln  Thr  Val  Asp  Ile  Trp  Ser
             195                      200                      205
```

```
Val  Gly  Cys  Ile  Met  Ala  Glu  Leu  Leu  Thr  Gly  Arg  Thr  Leu  Phe  Pro
     210                 215                      220

Gly  Thr  Asp  His  Ile  Asn  Gln  Leu  Gln  Gln  Ile  Met  Arg  Leu  Thr  Gly
225                      230                      235                      240

Thr  Pro  Pro  Ala  Tyr  Leu  Ile  Asn  Arg  Met  Pro  Ser  His  Glu  Ala  Arg
                    245                      250                      255

Asn  Tyr  Ile  Gln  Ser  Leu  Thr  Gln  Met  Pro  Lys  Met  Asn  Phe  Ala  Asn
                260                      265                      270

Val  Phe  Ile  Gly  Ala  Asn  Pro  Leu  Ala  Val  Asp  Leu  Leu  Glu  Lys  Met
               275                 280                      285

Leu  Val  Leu  Asp  Ser  Asp  Lys  Arg  Ile  Thr  Ala  Ala  Gln  Ala  Leu  Ala
          290                 295                      300

His  Ala  Tyr  Phe  Ala  Gln  Tyr  His  Asp  Pro  Asp  Asp  Glu  Pro  Val  Ala
305                      310                      315                      320

Asp  Pro  Tyr  Asp  Gln  Ser  Phe  Glu  Ser  Arg  Asp  Leu  Leu  Ile  Asp  Glu
                    325                      330                      335

Trp  Lys  Ser  Leu  Thr  Tyr  Asp  Glu  Val  Ile  Ser  Phe  Val  Pro  Pro  Pro
               340                 345                      350

Leu  Asp  Gln  Glu  Glu  Met  Glu  Ser
          355                      360
```

( 2 ) INFORMATION FOR SEQ ID NO:13:

( i ) SEQUENCE CHARACTERISTICS:
      ( A ) LENGTH: 1423 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Homo sapiens
      ( G ) CELL TYPE: Monocyte ( i x ) FEATURE:
      ( A ) NAME/KEY: CDS
      ( B ) LOCATION: 227..1309

( x i ) SEQUENCE DESCRIPTION: SEQ ID NO:13:

```
CCACTCCTGG  TATAATCTCG  CCCCAGTCGC  AGGGGCACAT  CCAGCCGCTG  CGGCTGACAG        60

CAGCCGCGCG  CGCGGGAGTC  TGCGGGGTCG  CGGCAGCCGC  ACCTGCGCGG  GCGACCAGCG       120

CAAGGTCCCC  GCCCGGCTGG  GCGGGCAGCA  AGGGCCGGGG  AGAGGGTGCG  GGTGCAGGCG       180

GGGGCCCCAC  AGGGCCACCT  TCTTGCCCGG  CGGCTGCCGC  TGGAAA ATG  TCT  CAG         235
                                                      Met  Ser  Gln
                                                       1

GAG  AGG  CCC  ACG  TTC  TAC  CGG  CAG  GAG  CTG  AAC  AAG  ACA  ATC  TGG  GAG    283
Glu  Arg  Pro  Thr  Phe  Tyr  Arg  Gln  Glu  Leu  Asn  Lys  Thr  Ile  Trp  Glu
          5                        10                       15

GTG  CCC  GAG  CGT  TAC  CAG  AAC  CTG  TCT  CCA  GTG  GGC  TCT  GGC  GCC  TAT    331
Val  Pro  Glu  Arg  Tyr  Gln  Asn  Leu  Ser  Pro  Val  Gly  Ser  Gly  Ala  Tyr
20                       25                       30                       35

GGC  TCT  GTG  TGT  GCT  GCT  TTT  GAC  ACA  AAA  ACG  GGG  TTA  CGT  GTG  GCA    379
Gly  Ser  Val  Cys  Ala  Ala  Phe  Asp  Thr  Lys  Thr  Gly  Leu  Arg  Val  Ala
               40                        45                       50

GTG  AAG  AAG  CTC  TCC  AGA  CCA  TTT  CAG  TCC  ATC  ATT  CAT  GCG  AAA  AGA    427
Val  Lys  Lys  Leu  Ser  Arg  Pro  Phe  Gln  Ser  Ile  Ile  His  Ala  Lys  Arg
                    55                       60                       65
```

```
ACC TAC AGA GAA CTG CGG TTA CTT AAA CAT ATG AAA CAT GAA AAT GTG          475
Thr Tyr Arg Glu Leu Arg Leu Leu Lys His Met Lys His Glu Asn Val
        70              75              80

ATT GGT CTG TTG GAC GTT TTT ACA CCT GCA AGG TCT CTG GAG GAA TTC          523
Ile Gly Leu Leu Asp Val Phe Thr Pro Ala Arg Ser Leu Glu Glu Phe
    85              90              95

AAT GAT GTG TAT CTG GTG ACC CAT CTC ATG GGG GCA GAT CTG AAC AAC          571
Asn Asp Val Tyr Leu Val Thr His Leu Met Gly Ala Asp Leu Asn Asn
100             105             110             115

ATT GTG AAA TGT CAG AAG CTT ACA GAT GAC CAT GTT CAG TTC CTT ATC          619
Ile Val Lys Cys Gln Lys Leu Thr Asp Asp His Val Gln Phe Leu Ile
                120             125             130

TAC CAA ATT CTC CGA GGT CTA AAG TAT ATA CAT TCA GCT GAC ATA ATT          667
Tyr Gln Ile Leu Arg Gly Leu Lys Tyr Ile His Ser Ala Asp Ile Ile
            135             140             145

CAC AGG GAC CTA AAA CCT AGT AAT CTA GCT GTG AAT GAA GAC TGT GAG          715
His Arg Asp Leu Lys Pro Ser Asn Leu Ala Val Asn Glu Asp Cys Glu
        150             155             160

CTG AAG ATT CTG GAT TTT GGA CTG GCT CGG CAC ACA GAT GAT GAA ATG          763
Leu Lys Ile Leu Asp Phe Gly Leu Ala Arg His Thr Asp Asp Glu Met
165             170             175

ACA GGC TAC GTG GCC ACT AGG TGG TAC AGG GCT CCT GAG ATC ATG CTG          811
Thr Gly Tyr Val Ala Thr Arg Trp Tyr Arg Ala Pro Glu Ile Met Leu
180             185             190             195

AAC TGG ATG CAT TAC AAC CAG ACA GTT GAT ATT TGG TCA GTG GGA TGC          859
Asn Trp Met His Tyr Asn Gln Thr Val Asp Ile Trp Ser Val Gly Cys
                200             205             210

ATA ATG GCC GAG CTG TTG ACT GGA AGA ACA TTG TTT CCT GGT ACA GAC          907
Ile Met Ala Glu Leu Leu Thr Gly Arg Thr Leu Phe Pro Gly Thr Asp
            215             220             225

CAT ATT GAT CAG TTG AAG CTC ATT TTA AGA CTC GTT GGA ACC CCA GGG          955
His Ile Asp Gln Leu Lys Leu Ile Leu Arg Leu Val Gly Thr Pro Gly
        230             235             240

GCT GAG CTT TTG AAG AAA ATC TCC TCA GAG TCT GCA AGA AAC TAT ATT          1003
Ala Glu Leu Leu Lys Lys Ile Ser Ser Glu Ser Ala Arg Asn Tyr Ile
245             250             255

CAG TCT TTG ACT CAG ATG CCG AAG ATG AAC TTT GCG AAT GTA TTT ATT          1051
Gln Ser Leu Thr Gln Met Pro Lys Met Asn Phe Ala Asn Val Phe Ile
260             265             270             275

GGT GCC AAT CCC CTG GCT GTC GAC TTG CTG GAG AAG ATG CTT GTA TTG          1099
Gly Ala Asn Pro Leu Ala Val Asp Leu Leu Glu Lys Met Leu Val Leu
                280             285             290

GAC TCA GAT AAG AGA ATT ACA GCG GCC CAA GCC CTT GCA CAT GCC TAC          1147
Asp Ser Asp Lys Arg Ile Thr Ala Ala Gln Ala Leu Ala His Ala Tyr
            295             300             305

TTT GCT CAG TAC CAC GAT CCT GAT GAT GAA CCA GTG GCC GAT CCT TAT          1195
Phe Ala Gln Tyr His Asp Pro Asp Asp Glu Pro Val Ala Asp Pro Tyr
        310             315             320

GAT CAG TCC TTT GAA AGC AGG GAC CTC CTT ATA GAT GAG TGG AAA AGC          1243
Asp Gln Ser Phe Glu Ser Arg Asp Leu Leu Ile Asp Glu Trp Lys Ser
325             330             335

CTG ACC TAT GAT GAA GTC ATC AGC TTT GTG CCA CCA CCC CTT GAC CAA          1291
Leu Thr Tyr Asp Glu Val Ile Ser Phe Val Pro Pro Pro Leu Asp Gln
340             345             350             355

GAA GAG ATG GAG TCC TGAGCACCTG GTTTCTGTTC TGTTGATCCC ACTTCACTGT         1346
Glu Glu Met Glu Ser
              360

GAGGGGAAGG CCTTTTCACG GGAACTCTCC AAATATTATT CAAGTGCCAA AAAGGTCCAG       1406

CAATTTCGTT ACTTATG                                                      1423
```

( 2 ) INFORMATION FOR SEQ ID NO:14:

( i ) SEQUENCE CHARACTERISTICS:
        ( A ) LENGTH: 360 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ser Gln Glu Arg Pro Thr Phe Tyr Arg Gln Glu Leu Asn Lys Thr
 1               5                  10                  15

Ile Trp Glu Val Pro Glu Arg Tyr Gln Asn Leu Ser Pro Val Gly Ser
             20                  25                  30

Gly Ala Tyr Gly Ser Val Cys Ala Ala Phe Asp Thr Lys Thr Gly Leu
         35                  40                  45

Arg Val Ala Val Lys Lys Leu Ser Arg Pro Phe Gln Ser Ile Ile His
     50                  55                  60

Ala Lys Arg Thr Tyr Arg Glu Leu Arg Leu Leu Lys His Met Lys His
 65                  70                  75                  80

Glu Asn Val Ile Gly Leu Leu Asp Val Phe Thr Pro Ala Arg Ser Leu
                 85                  90                  95

Glu Glu Phe Asn Asp Val Tyr Leu Val Thr His Leu Met Gly Ala Asp
             100                 105                 110

Leu Asn Asn Ile Val Lys Cys Gln Lys Leu Thr Asp Asp His Val Gln
         115                 120                 125

Phe Leu Ile Tyr Gln Ile Leu Arg Gly Leu Lys Tyr Ile His Ser Ala
     130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                 165                 170                 175

Asp Glu Met Thr Gly Tyr Val Ala Thr Arg Trp Tyr Arg Ala Pro Glu
             180                 185                 190

Ile Met Leu Asn Trp Met His Tyr Asn Gln Thr Val Asp Ile Trp Ser
         195                 200                 205

Val Gly Cys Ile Met Ala Glu Leu Leu Thr Gly Arg Thr Leu Phe Pro
     210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                 245                 250                 255

Asn Tyr Ile Gln Ser Leu Thr Gln Met Pro Lys Met Asn Phe Ala Asn
             260                 265                 270

Val Phe Ile Gly Ala Asn Pro Leu Ala Val Asp Leu Leu Glu Lys Met
         275                 280                 285

Leu Val Leu Asp Ser Asp Lys Arg Ile Thr Ala Ala Gln Ala Leu Ala
     290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                 325                 330                 335

Trp Lys Ser Leu Thr Tyr Asp Glu Val Ile Ser Phe Val Pro Pro Pro
             340                 345                 350

Leu Asp Gln Glu Glu Met Glu Ser
```

-continued 3 5 5 3 6 0

( 2 ) INFORMATION FOR SEQ ID NO:15:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

CGCCCTCGAG ATGTCTCAGG AGAGGCCCAC G 31

( 2 ) INFORMATION FOR SEQ ID NO:16:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GCCAGTCCAA AATCCAGAAT C 21

OLIGONUCLEOTIDES COMPRISING A REGION OF A CYTOKINE SUPPRESSIVE ANTI-INFLAMMATORY DRUG BINDING PROTEIN

CROSS-REFERENCE TO RELATED APPLICATION

This application is a continuation-in-part application of U.S. application Ser. No. 08/250,975 filed May 31, 1994 which is a continuation-in-part application of U.S. application Ser. No. 08/123,175, filed Sep. 17, 1993, now abandoned, the contents of which are incorporated herein by reference.

FIELD OF THE INVENTION

This invention relates to drug binding proteins, to genes encoding same and to assays and methods for screening pharmaceuticals. More specifically, this invention relates to Cytokine Suppressive Anti-Inflammatory Drug (CSAID) binding proteins, to genes encoding same and to assays and screens useful in the evaluation and characterization of drugs of this pharmacologic class.

BACKGROUND OF THE INVENTION

Cytokines play an important role in regulating the cellular response during inflammation and other immune functions. Of particular interest are the cytokines interleukin-1 (IL-1, $\alpha$ and $\beta$) and tumor necrosis factor (TNF, $\alpha$ and $\beta$), which are the intercellular proteins involved in the initial step of the inflammatory response cascade (Arai, et al., *Ann. Rev. Biochem.* 59: 783–836 (1990)). Thus, there has been a substantial amount of research recently devoted to interfering with the production of IL-1 and TNF in response to an inflammatory stimulus.

One therapeutic approach involves suppressing the production of IL-1 and TNF at the level of transcription and/or translation and/or secretion. The activities associated with certain of pyridinyl imidazoles led to a class of compounds referred to as "CSAIDs", or Cytokine Suppressing Anti-Inflammatory Drugs (FIG. 1). These compounds appear to arrest the expression of IL-1 and TNF predominantly at the translational level, although a lesser effect on transcription has also been observed but effects on other steps cannot be ruled out.

The pyridinyl imidazole, 5-(4-pyridyl)-6(4-fluorophenyl)-2,3-dihydroimidazo(2,1-b)thiazole (SK&F 86002) was identified as the prototypic CSAID. The basis for its activity has been established and characterized (Lee, et al., *Int'l. J. Immunopharm.* 10(7): 835–843 (1988); *Agents and Actions* 27(¾): 277–279 (1989) and *Int'l. J. Immunother.* 6(1):1–12 (1990)). SAR studies (discussed herein) suggest that cytokine suppressive effect of the pyridinyl imidazoles represents a unique activity independent of their inhibitory effects on eicosanoid and leukotriene production. However, no compound of the initial series was selective for cytokine suppressive activity or was particularly potent.

Since the CSAIDs have substantial potential as novel anti-inflammatory therapeutic agents, there is significant interest in characterizing their mechanism of action at the molecular level, as well as obtaining compounds with increased selectivity and potency. Specifically, identification and characterization of the CSAID molecular target would enhance the understanding of the biochemical processes involved in inflammation and aid in the design and screening of more potent anti-inflammatory drugs. This invention discloses, inter alia, the purification and characterization of such CSAID binding proteins (CSBPs).

The DNAs of this invention, such as the specific sequences disclosed herein, are useful in that they encode the genetic information required for the expression of the novel CSBPs. Additionally, the sequences may be used as probes in order to isolate and identify any additional members of the CSBP family as well as forming the basis of antisense therapy for disease conditions which are characterized by atypical expression of the CSBP gene. The novel protein itself is useful directly as a therapeutic or diagnostic agent as well as a component in a screening system for compounds which are antagonists or agonists of CSAID binding activity. The protein is also useful for eliciting antibody production in heterologous species, said antibodies being useful for the aforesaid diagnostic, therapeutic and screening applications. These and additional uses for the reagents described herein will become apparent to those of ordinary skill in the art upon reading this specification.

BRIEF DESCRIPTION OF THE INVENTION

This invention provides isolated nucleic acid molecules encoding a CSAID binding protein, including mRNAs, DNAs, cDNAs as well as antisense analogs thereof and biologically active and diagnostically or therapeutically useful fragments thereof.

This invention also provides recombinant vectors, such as cloning and expression plasmids useful as reagents in the recombinant production of CSAID binding proteins or peptides, as well as recombinant prokaryotic and/or eukaryotic host cells comprising the CSBP encoding nucleic acid sequence.

This invention also provides methods of identifying ligands capable of binding to the CSBP by measuring the binding of the ligand to be identified relative to known ligands.

This invention also provides methods for screening drugs to identify compounds which interact with and bind to the CSBP. The binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in screening protocols. Regardless of the form of the binding protein, a plurality of compounds are contacted with the binding protein under conditions sufficient to form a compound/binding protein complex and compound capable of forming, enhancing or interfering with said complexes are detected.

This invention also provides nucleic acid probes comprising nucleic acid molecules of sufficient length to specifically hybridize to CSAID binding protein-like sequences.

This invention also provides an antisense oligonucleotide having a sequence capable of binding with mRNAs encoding the CSBP so as to prevent the translation of said mRNA.

This invention also provides transgenic non-human animals comprising or lacking a nucleic acid molecule encoding a CSBP. Also provided are methods for use of said transgenic animals as models for differential binding protein expression, mutation and SAR evaluation as well as in ligand and drug screens.

This invention also provides fusion proteins comprising a CSAID binding domain and a binding protein/ligand binding indicator domain capable of providing an analytically detectable signal. Also provided are methods of screening drugs by forming, enhancing or interfering with the detectable signal.

This invention also provides a method of screening compounds to identify those compounds which bind to a CSAID binding protein comprising: providing a recombinant host cell expressing on the surface thereof a CSAID binding protein, said protein being associated with a second component capable of providing a detectable signal in response to the binding of a compound to said protein; contacting a plurality of candidate compounds with said host cells under conditions sufficient to permit binding of compounds to the binding protein; and identifying those compounds capable of binding by detecting the signal produced by said second component.

BRIEF DESCRIPTION OF THE FIGURES

FIG. 13 illustrates the nucleic acid sequence (SEQ ID NO:6) and amino sequence (SEQ ID NO:7) of a portion of the CSAIDs Binding Protein.

FIG. 14 illustrates the nucleic acid sequence (SEQ ID NO:8) of a second portion of the CSAIDs Binding Protein.

FIG. 16 illustrate the cDNA (nucleotides 356–1467 of SEQ ID NO: 11) and amino acid (SEQ ID NO:12) sequence of one of the CSBPs disclosed herein.

FIG. 17 illustrates the difference in nucleotide (nucleotides 1054 to 1128 of SEQ ID NOs: 11 and 13) and amino acid (amino acids 230 to 255 of SEQ ID NOs: 12 and 14) sequence between CSBP-1 and CSBP-2.

FIG. 19 illustrates the alignment of the amino acid sequences of CSBP-1 (SEQ ID NO:12) and CSBP-2 (SEQ ID NO:14) with selected members of the protein kinase family.

FIGS. 21A–E illustrate the full length nucleic acid sequence of CSBP-1 cDNA (SEQ ID NO:11).

FIGS. 22A–22B illustrate the full length nucleic acid sequence of CSBP-2 cDNA (SEQ ID NO:13).

DETAILED DESCRIPTION OF THE INVENTION

Figure 1:
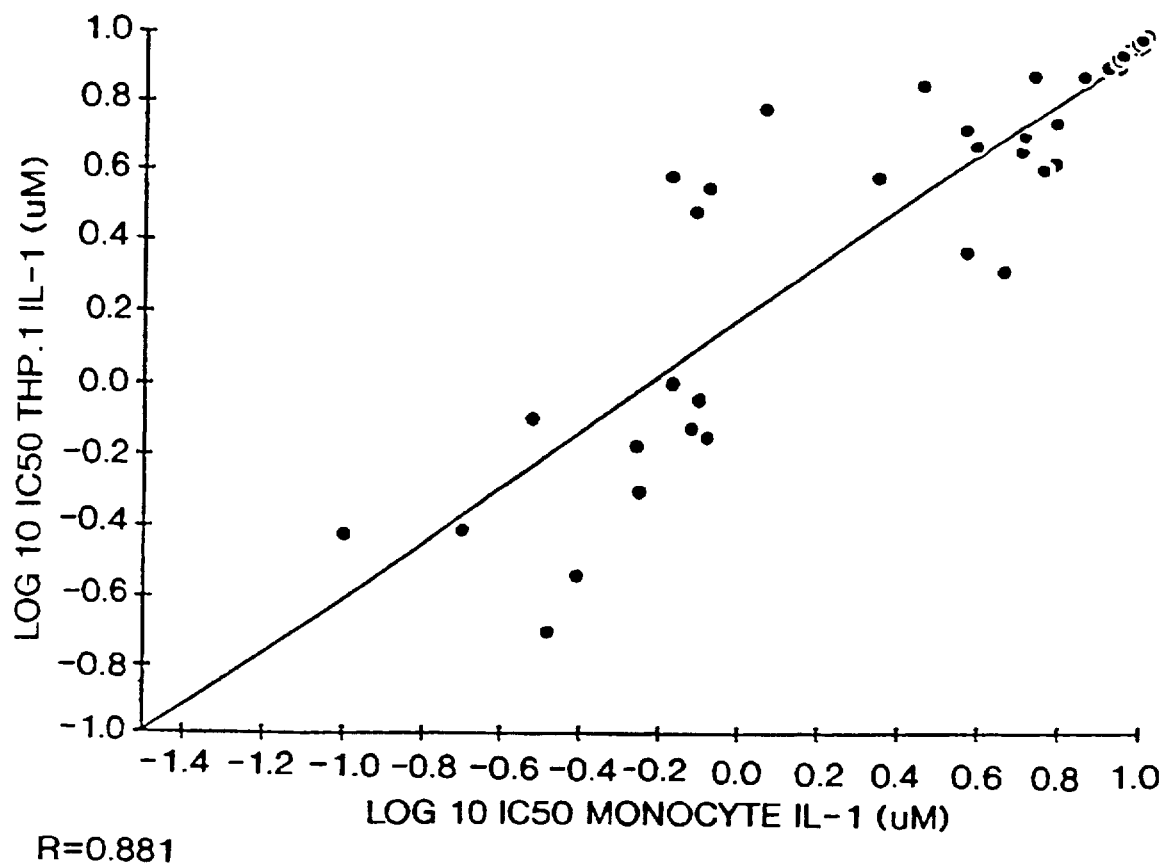
FIG. 1 illustrates the correlation of $IC_{50}$ of the pyridinyl imidazole CSAIDs for IL-1β biosynthesis in THP.1 cells and human monocytes. A Log-Log scatter plot of ~50 compounds with regard to their $IC_{50}$s for inhibiting IL-1 or TNF was generated. Regression analysis was performed and the correlation coefficient is 0.881.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

"Fusion protein" is a protein resulting from the expression of at least two operatively-linked heterologous coding sequences. The protein comprising a CSAIDs binding protein or fragment thereof and a second unrelated peptide sequence is an example of a fusion protein.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience, Ausbel, et al. (ed.) (1992). Protein sequences that are substantially the same can be identified by proteolytic digestion, gel electrophoresis and microsequencing.

The term "functionally equivalent" with respect to CSBP intends that the amino acid sequence of the subject protein is one that will display the CSAIDs binding activity disclosed herein.

A "heterologous" region of a DNA construct is an identifiable segment of DNA within or attached to another DNA molecule that is not found in association with the other molecule in nature. Thus, when the heterologous region encodes a receptor gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation, alternative splicing or naturally occurring mutational events do not give rise to a heterologous region of DNA, as used herein.

Development of Molecular Reagents:
Radioligand Synthesis

In order to isolate and purify the CSBP of this invention, it was first necessary to provide several labeled molecular reagents. The phenolic triaryl imidazole, Compound I, was chosen as an alternative radioligand because of its nanomolar potency and the relative ease of synthesis of the radiolabeled compound through catalytic reduction of the corresponding aryl bromide in the presence of tritium gas.

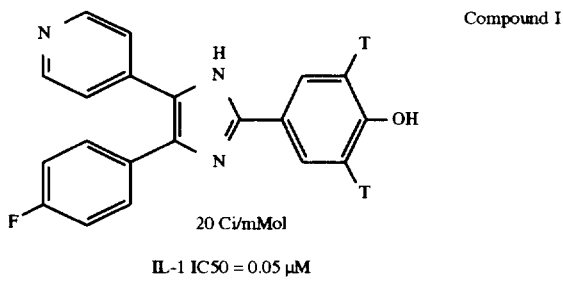

Compound I

20 Ci/mMol

IL-1 IC50 = 0.05 μM

Compound I was prepared according to the following reaction protocol:

Preparation of 4-(Fluorophenyl)-2-(4-hydroxyphenyl-3,5-$t_2$)-5-(4-pyridyl)imidazole, (Compound I).

A 2.9 mg (0.0059 mmol) portion of 2(3,5-Dibromo-4-hydroxyphenyl)-4-(4-fluorophenyl)-5-(4-pyridyl)imidazole, Compound I(p), was dissolved in 0.95 mL of dry DMF and 0.05 mL of triethylamine in a 2.4 mL round bottom flask equipped with a small magnetic stirring bar. A 1.7 mg portion of 5% Pd/C (Engelhard lot 28845) was added, and the flask was attached to the stainless steel tritium manifold. The mixture was degassed through four freeze-pump-thaw cycles, then tritium gas (5.3 Ci, 0.091 mmol) was introduced. The reaction mixture was allowed to warm to room temperature and was stirred vigorously for 20 h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were removed by static vacuum transfer. A 1.5 mL portion of methanol was added to the residue, then removed by static vacuum transfer. The latter process was repeated. Finally, the residue was suspended in

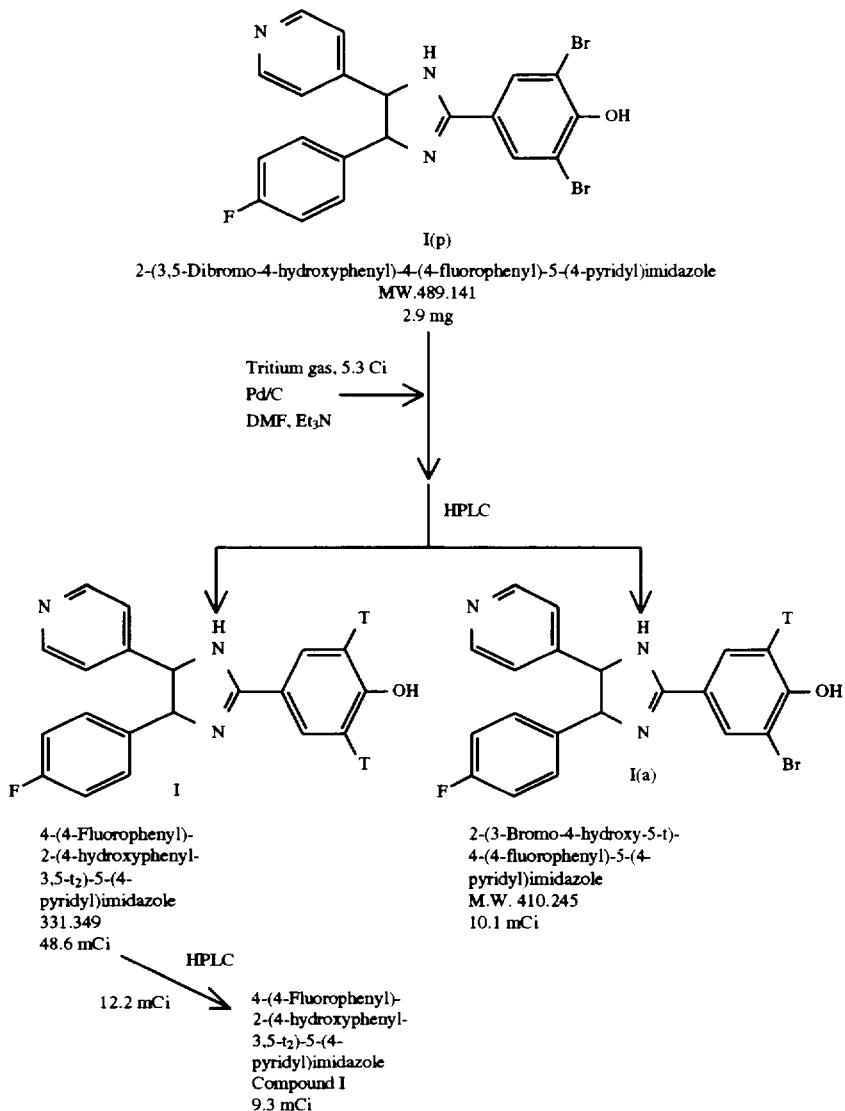

1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Partisil 5 ODS-3, 4.6 mm I.D.×25 cm, 1 mL/min of 70:30:0.1 water/acetonitrile/ trifluoroacetic acid, Radiomatic Flo-One Beta radio detector with 3 mL/min of Ecoscint-H cocktail through a 0.75 ML cell) showed the presence of Compound I ($R_t$=60 min, ca. 37% of total radioactivity), and a discrete intermediate presumed to be the monobromo derivative Compound Ia ($R_t$=11.8 min, ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia and SB collected separately.

| HPLC Method | |
|---|---|
| Column | Altex Ultrasphere 10 mm I.D. × 25 cm |
| Mobile Phase | 70:30:0.1 water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I 24 min Compound Ia |

The pooled Compound I fractions totaled 32 mL in volume and the radioactive concentration was 1.52 mCi/mL (total 48.6 m Ci). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness in vacuo at <35° C., then redissolved in 0.5 mL of mobile phase. The whole volume was injected into the HPLC system described above, and the appropriate peak was collected. Evaporation of the collected eluate in vacuo at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in $CD_3OD$.

Analysis of 4-(4-Fluorophenyl)-2-(4-hydroxyphenyl-3,5-$t_2$)-5-(4-pyridyl)imidazole, Compound I.

| Radiochemical Purity by HPLC | |
|---|---|
| Method | |
| Column | Ultrasphere Octyl, 5 μm, 4.6 mm I.D. × 25 cm, Beckman |
| Mobile Phase | 350:150:0.5 (v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count (Tru-Lab Supply Co.) |
| Flow rate | 5.0 mL/min |
| Cell volume | 0.75 mL |
| Retention time | 7.7 min |
| Result | 98.7 |

| Radioactive Concentration by Scintillation Counting | |
|---|---|
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |
| Specific Activity by Mass Spectrometry | |
| Method | CI-MS, $NH_3$ reagent gas |
| Result | 20.0 Ci/mmol |
| | $^3$H Distribution: |
| | Unlabeled 44% |
| | Single Label 43% |
| | Double Label 13% |
| | $^3$H NMR[9] |
| Method | |
| Instrument | Brunker AM 400 |
| Experiment | Proton decoupled $^3$H NMR Proton non-decoupled $^3$H NMR Proton non-decoupled $^3$H NMR |
| Peak Referencing | Solvent Peak of methanol ∂ 3.3 |
| Solvent | Methanol-$d_4$ |
| Result | Tritium is incorporated exclusively on the carbon atoms ortho to aromatic hydroxyl group |

| Analytical Summary | |
|---|---|
| Assay | Result |
| Radiochemical purity determined by HPLC | 98.7% |
| Radioactivity concentration determined by scintillation counting | 2.44 mCi/mL |
| Specific activity determined by mass spectrometry | 20.0 Ci/mmol |
| $^3$H NMR | agrees with the proposed structure |

Photoaffinity Radiolabeled Ligand

Additionally, a photoaffinity radiolabel was synthesized. Ideally, the radiophotoaffinity reagent should have a submicromolar binding affinity, a convenient site for the attachment of a radiolabel (preferable a gamma emitter) and allow for the positioning of the photoreactive group, (e.g. an azide) proximal to the binding site. The SAR leading to the proposal of Compound IV as the candidate for the photoaffinity reagent is illustrated in Table I below.

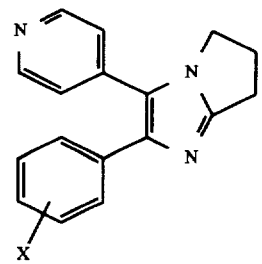

Formula II

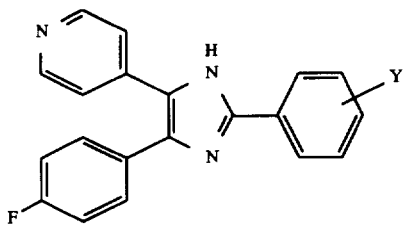

Formula III

TABLE I

| Compound | X | BioAssay IC50, µM | Compound | Y | BioAssay IC50, µM |
|---|---|---|---|---|---|
| IIa | 4-F | >0.1 | IIIa | H | 0.15 |
| IIb | 4-H | 0.5 | IIIb | 4-N$_3$ | 0.05 |
| IIc | 4-Cl | 0.05 | IIIc | 3-I-4-NH$_2$ | 0.48 |
| IId | 3-Cl | 0.04 | IIId | 4-NH$_2$ | 0.28 |
| IIe | 2-Cl | 0.25 | | | |
| IIf | 4-I | 0.58 | | | |
| IIg | 3-I | 0.05 | | | |

In addition, a specific ELISA assay may also be usefully employed to determine IL-1β and TNFα levels (see: PCT Applications US93/00674 and US93/00675)

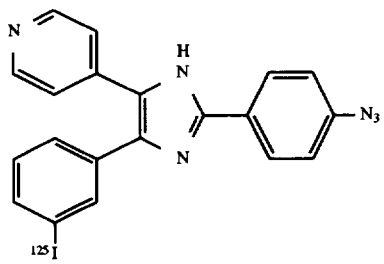

Compound IV

CSAIDs binding IC$_{50}$ = 0.72 µM

The synthesis of radioiodinated photoaffinity label, Compound IV, employed a palladium-mediated stannylation of the aryl iodide and subsequent electrophilic radioiodination, according to the following protocol.

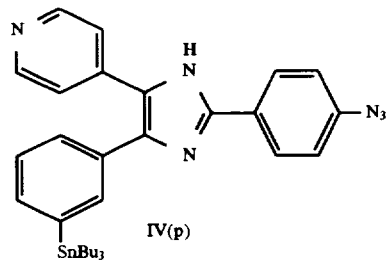

IV(p)

[3-[2-(4-azidophenyl)-5-(4-pyridinyl)-1H-(4-pyridinyl)-imidazol-4-yl)]phenyl]phenyl]tributylstannane
M.W.627.40
Compound IV(p)
250 µg

| Na$^{125}$I | Chronic-T 3% HOAc in EtO |

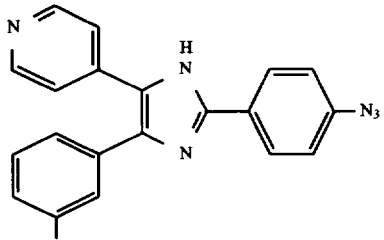

4-[2-(4-azidophenyl)-5-(3-$^{125}$Iodo-phenyl)-1H-imidazol-4-yl]pyridine
Compound IV
3.60 mCi Process Description Synthesis and purification of 4-[2-(4-azidophenyl)-5-(3-$^{125}$Iodo-phenyl)-1H-imidazol-4-yl]pyridine.

[3-[2-(4-Azidophenyl)-5-(4-pyridinyl)-1H imidazol-4-yl] phenyl]-tributylstannane. Compound IV (p) (250 µg, 0.398 µmol, was dissolved in 100 µL of 3% acetic acid in ethanol. To this solution was added 2.85 µg of chloramine-T hydrate (0.013 µmol) in 11.4 µL of water and 5.19 mCi of sodium [$^{125}$I]iodine in 45 µL of 0.1N sodium hydroxide. Another 50 µL of 3% acetic acid in ethanol was added to make the reaction mixture homogeneous. The reaction was stirred 60 minutes at room temperature (in the dark). The reaction was then blown to dryness under a stream of dry nitrogen and the residue partitioned between chloroform (1 mL) and saturated aqueous sodium bicarbonate (1 mL). The aqueous layer was extracted with chloroform (2×1 mL), the organic layers were combined and dried by passing through a pipet filled with granular sodium sulfate. The solvent was removed under stream of dry nitrogen; the residue was found to contain 4.36 mCi of iodine-125 (assayed on the Capintec dose calibrator). The aqueous layers were found to contain 310 µCi of iodine-125. The residue from the organic layer was taken up in 80 µL of HPLC mobile phase and purified on a Baker SiO$_2$ column, 5 µm, 4.6 mm I.D.×250 mm, eluted at 1.5 mL/min with 90:10:1 (v/v/v) hexane, isopropanol/triethylamine, with UV monitoring at 260 nm. The product fractions were combined and blown to dryness under a stream of dry nitrogen. The product was taken up in 3.0 mL of absolute ethanol. This procedure gave 3.60 mC of Compound IV at a radiochemical purity of 99.0%, radio active concentration of 1.20 mCi/mL and a specific activity of 1736 Ci/mmol.

Analysis of 4-[2-azidophenyl)-5-(3-iodo-$^{125}$I-phenyl) 1H-imidazol-4-yl]pyridine, Compound IV.

| Radiochemical Purity by HPLC | |
|---|---|
| Method | |
| Column | Baker, Silica, 5 µm, 120 A, 4.6 mm I.D. × 25 cm. |
| Mobile Phase | 90:10:1 (v/v/v) hexane/isopropanol/triethylamine |
| Flow Rate | 1.3 mL/min |
| Mass detection | UV at 260 nm |
| Radioactivity detection | |
| Detector | β-RAM radioactivity flow detector |
| Scintillator | Tru-Count (Tru-Lab Supply Co.) |
| Flow rate | 5.0 mL/min |
| Cell size | 0.8 mL |
| Retention time | 17.0 min |
| Result | 99.0% |

-continued

Mass Concentration by HPLC

Method

| | |
|---|---|
| Column | Baker, Silica, 5 µm, 120 A, 4.6 mm I.D. × 25 cm. |
| Mobile Phase | 90:10:1 (v/v/v) hexane/isopropanol/triethylamine |
| Flow Rate | 1.5 mL/min |
| Mass detection | UV at 260 nm |
| Retention time | 11.2 min |
| Result | 99.0% |

Radioactive Concentration by Scintillation
Counting - external standard method

Method

| | |
|---|---|
| Solvent | Ready Safe (Beckman) |
| Instrument | TM Analytic model 6881 |
| Efficiency | Automated DPM calculation from quench curve |
| Result | 1.2 mCi/mL |

Specific Activity Derived from Mass and Radioactive Concentrations

| | |
|---|---|
| Method | derived from mass and radioactive concentrations |
| Result | 1736 Ci/mmol |

Analytical Summary

| Assay | Result |
|---|---|
| Radiochemical purity by HPLC | 99.0% |
| Massive concentration by HPLC | 0.32 µg/mL |
| Radioactive concentration | 1.2 mCi/mL |
| Specific activity derived from mass and radioactive concentrations | 1736 Ci/mmol |

The photoaffinity label has an $IC_{50}$ of 0.5–0.8 µM in a competitive binding assay and $IC_{50}$ of 3 µM in a CSAIDs bioassay.

CSAIDs Bioassay

The biological assay employed to evaluate CSAIDs activity was the IL-1 dependent EL-4/IL2 induction assay (Simon. P. L. et al. *J. Immuno. Meth.* 84: 85–94 (1985)). Briefly. Human monocytes were plated in 24-well plates in LPS-free RPMI 1640 media containing 1% human AB serum at a concentration of $10^6$ per milliliter per well and allowed to adhere for 1 h at 37° C.; non-adherent cells were removed by gentle washing. Test compounds or media were added to the cells 0 or 1 h before the addition of bacterial lipopolysaccharide (*E. coli* 001:B4; Difco, Detroit) at 10 ng/ml. The cultures were then incubated at various intervals as indicated at 37° C. in a humidified 5% $CO_2$ atmosphere. At the end of the incubation period, culture supernatants were collected. The residual adherent monocytes were lysed in a buffer containing 0.15M octyl-glucopyranoside, 25 mM Hepes, and 0.5 mM phenylmethylsulfonylfluoride in saline. Both supernatants and cell lysates were clarified by centrifugation and assayed for IL-1 activity.

IL-1 activity was measured by its ability to stimulate the secretion of IL-2 by EL-4 (ATCC TIB181) cells in the presence of A23187 ionophore. Serial dilutions of the samples were incubated with $10^5$ EL-4 cells in the presence of $2\times10^{-7}$M calcium ionophore A23187. After overnight incubation, 0.1 ml of a cell-free supernatant from each culture was taken and incubated with $10^4$ IL-2-dependent CTLL-20 (ATCC-TIB214) cells. Following an additional 20 hours of incubation, the cultures were pulsed with 1 µCi of tritiated thymidine for 4 h. The cells were then harvested onto glass-fibre filters and the radioactivity determined by liquid scintillation counting. All determinations of IL-1 activity were made in comparison to a standard.

CSAIDs Binding Assay

The next phase of the isolation and purification of CSBP required the development and validation of a cell-based CSAIDs binding assay. As mentioned above the early CSAID studies were conducted in human monocytes. A more convenient cell source, the human monocytic leukemia cell line, THP.1. (ATCC TIB 202) was selected and was shown to be an adequate surrogate cell source for mechanistic studies by virtue of its response to stimuli to produce IL-1 and TNF as well as a sensitivity towards CSAIDs comparable to human monocytes (FIG. 1).

Figure 2:
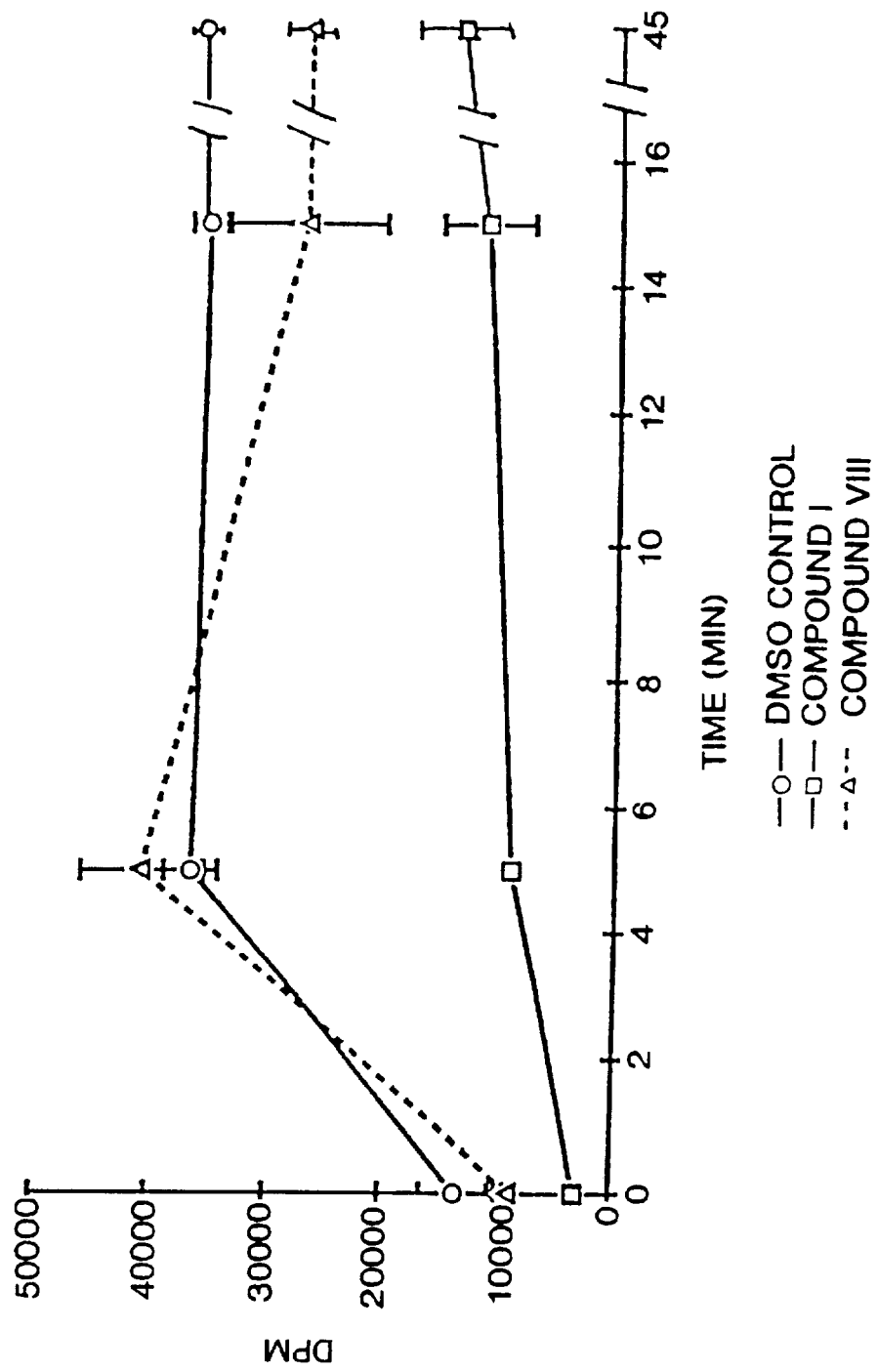
FIG. 2 illustrates the time dependent and reversible uptake of $^3$H-Compound I in intact THP.1 cells. 2 million THP.1 cells were incubated alone (appropriate solvent control) or with radiolabeled Compound I (50 nM) in the absence (0—0) or presence of excess non-radioactive ligand (50 μM) Compound I (square) and Compound VIII (triangle). At various intervals, the cells were centrifuged over a 8% sucrose cushion and the cell pellet was assessed for radioactivity by scintillation counting. Saturable binding was achieved at 15 minutes.

Radiolabeled Compound I was taken up by intact THP.1 cells in a time-dependent manner (FIG. 2). The uptake of the radiolabel was rapid and reached a maximum level at 3–5 minutes at 37° C. In addition, the uptake of radiolabel was saturable and specific.

Figure 3:
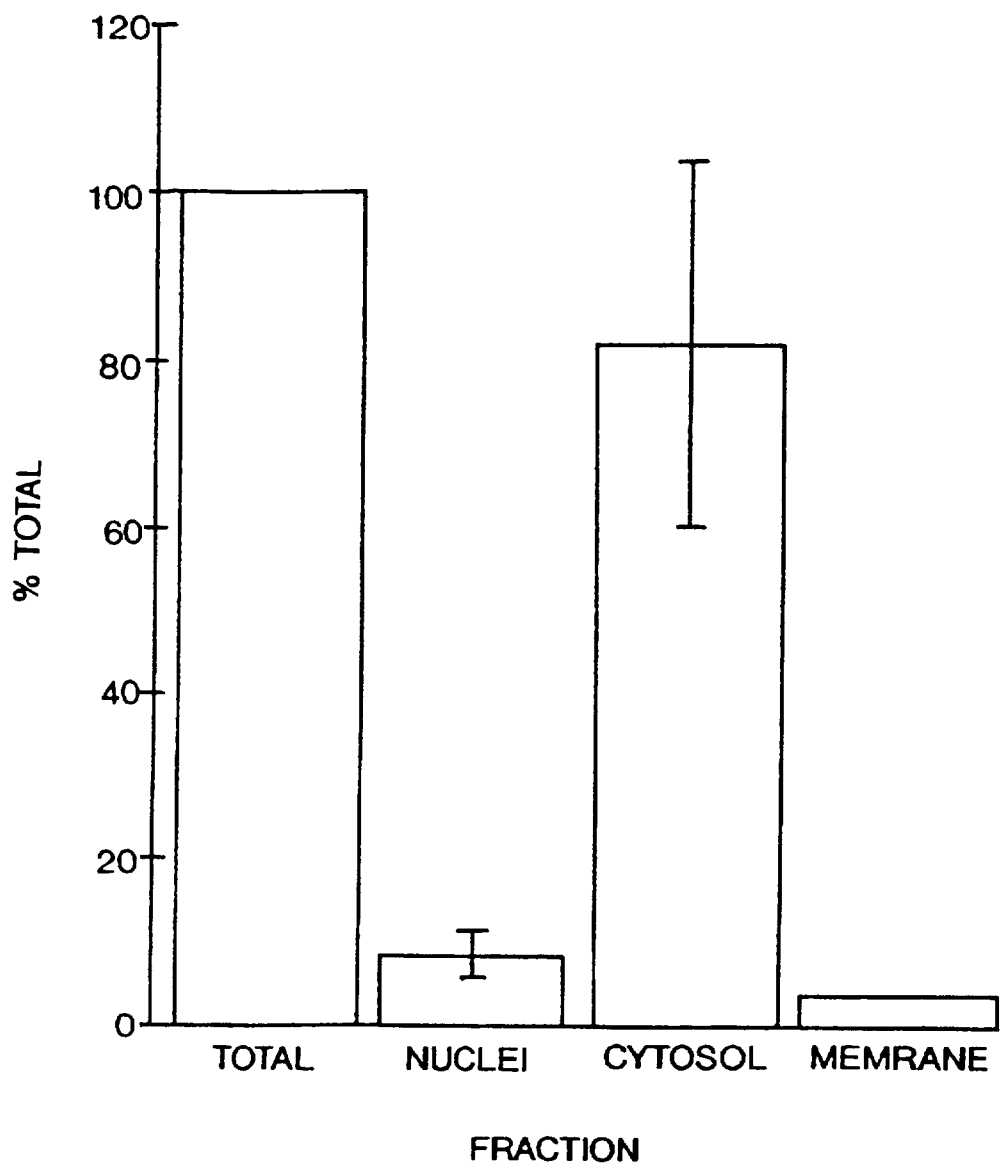
FIG. 3 illustrates the subcellular localization of binding activity. 10 million THP.1 cells were incubated with 50 nM radiolabeled Compound I for 30 minutes at 22° C. The cells were disrupted by dounce homogenization. The cell lysate was fractionated into nuclear, particulate and soluble fraction by differential centrifugation. The bulk of radioactivity was associated with the cytosolic fraction. An identical result was obtained in a binding assay using previously fractionated samples.

Upon subcellular fractionation of radiolabeled ligand loaded THP.1 cells, the predominant subcellular site of accumulation of the radioactivity was found to be the cytosol. (FIG. 3).

A specific and reproducible CSAID binding assay was developed using soluble cytosolic fraction from THP.1 cells and radiolabeled Compound I. In brief, THP.1 cytosol was routinely prepared from cell lysate obtained by nitrogen cavitation followed by a 10K×g low speed and a 100K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 µMβ-mercaptoethanol, $NaN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present.

More specifically, the CSAID Binding Assay is performed as follows:

Materials:

Incubation buffer: 20 mM Tris. 1 mM $MgCl_2$, 20 µM Hepes, 0.02% $NaN_3$, store at 4° C. Elution buffer: 20 mM Tris, 50 µM 2-mercaptoethanol, $NaN_3$, store at 4° C.

G-10 Sephadex: add 100 g Sephadex G-10 (Pharmacia, Uppsala, Sweden) to 400 mL dd $H_2O$ and allow to swell at room temperature for 2 hours. Decant fines and wash 3 times. Add $NaN_3$ and QS with dd $H_2O$ to 500 mLs and store at 4° C.

Assemble Columns: Straw column, filter frit and tip (Konotes, SP 420160-000, 420162-002). Lowsorb tubes (Nunc) used in binding reaction. THP.1 cytosol spun at 15000 rpm for 5 min to clarify. THP.1 cytosol prepared by hypnotic treatment of cells and lysis by decompression in nitrogen. Nuclei and membrane fragments removed by differential centrifugation (10.000 g for 1 hour and 100.000 g for 1 hour).

Compounds: Non-radioactive Compound I with corresponding EtOH control (dilutions made in incubation buffer) and $^3$H-Compound I (dilutions in incubation buffer)

Method:

A. Column Preparation

1. Begin 30 min before anticipated elution of reaction mixture.

2. Add 3 mL of G-10 slurry to column for bed vol of 1.5 ml.

3. Rinse with 7 mL elution buffer (fill to top of column)

4. Cut columns down to size.

B. Sample Incubation
1. 15 min incubation at 4° C.
2. Binding reaction mixture; 100 μL cytosol, 10 μL cold Compound I or EtOH control, 10 μL $^3$H-Compound I (molar concentration depends on nature of study).
3. "Free" control=100 μL incubation buffer in lieu of cytosol preparation.

C. Sample Elution
1. Elute at 4° C.
2. Add total reaction volume to G-10 column.
3. Add 400 μL elution buffer to column and discard eluate.
4. Add 500 μL elution buffer to column, collecting eluted volume in 20 ml scintillation vial.
5. Add 15 mL Ready Safe scintillation fluid.
6. Vortex and count in liquid scintillation counter for 5 minutes. Include a "total input counts control" (10 μL of labeled ligand).

D. Data Analysis
1. Plot DPMS as ouptut in graphic form and analyze by regression analysis and "Lundon ligand binding" software for the determination of IC 50 and Kd/Ki respectively.
2. Rank order the IC50s of the tested compounds in the CSAID bioassay and compare to that generated by the CSAID binding assay and establish a correlation curve.

Figure 4A:
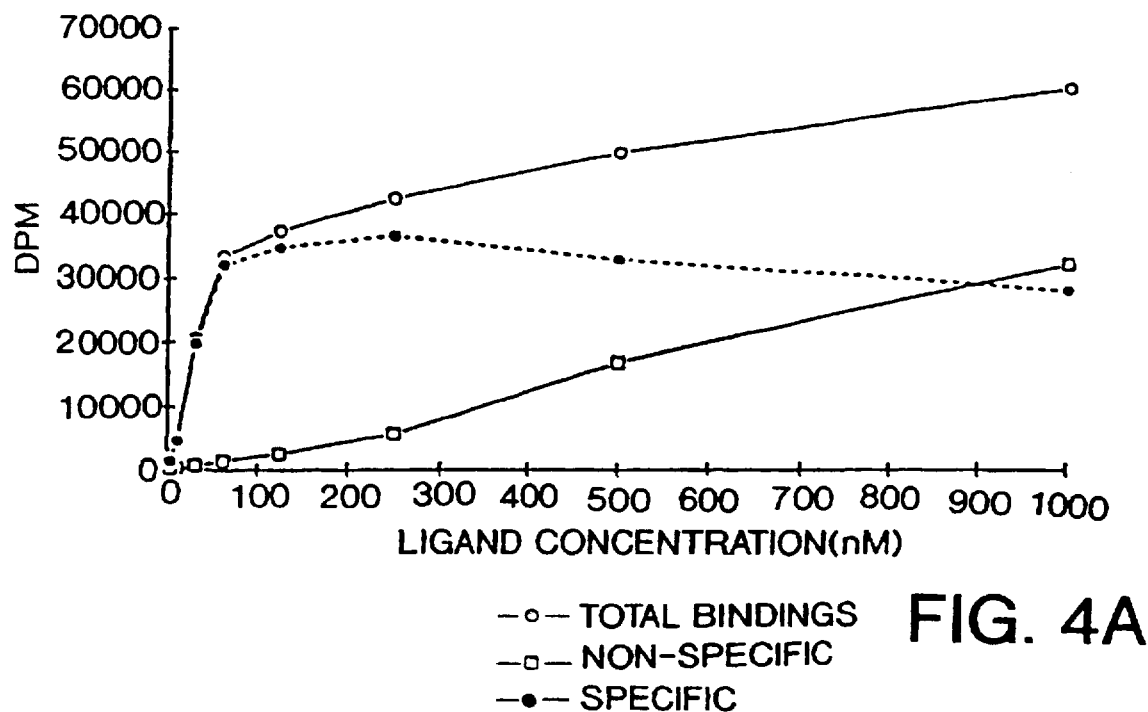
FIGS. 4A–4B illustrate the binding isotherm and Scatchard plot analysis of Compound I binding by THP.1 cytosol. Titration of radiolabeled Compound (0 to 1 μM) in the presence of constant excess cold ligand (50 μM) was performed in the binding assay using crude THP.1 cytosol. The specific binding is saturable. Scatchard plot analysis demonstrated a Kd of 3.6 nM. Bmax of 5 pmol/mg protein and a single site binding.
Figure 4B:
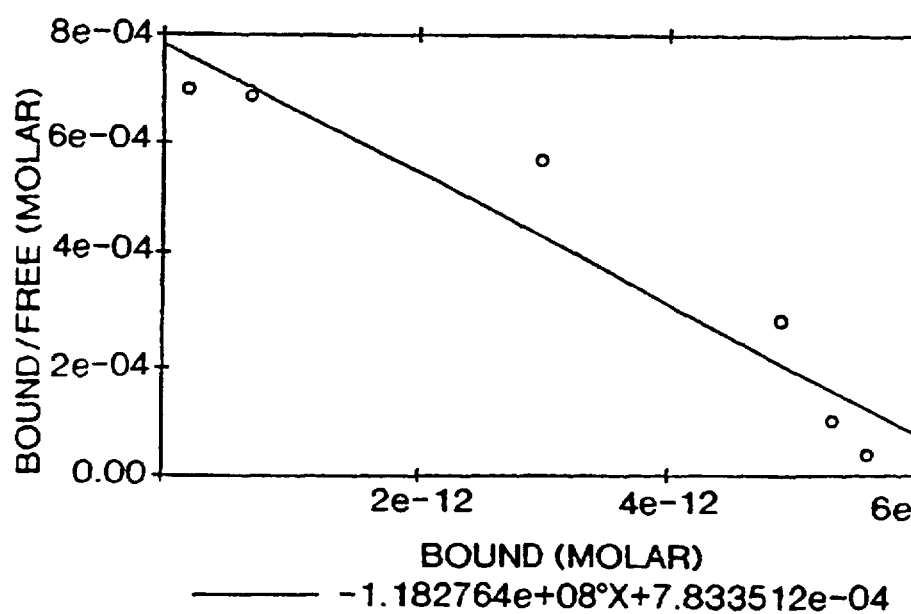

The binding assay was further validated by the following criteria:

THP.1 cytosol demonstrated saturable and specific binding of radiolabeled Compound I (FIG. 4).

Figure 5:
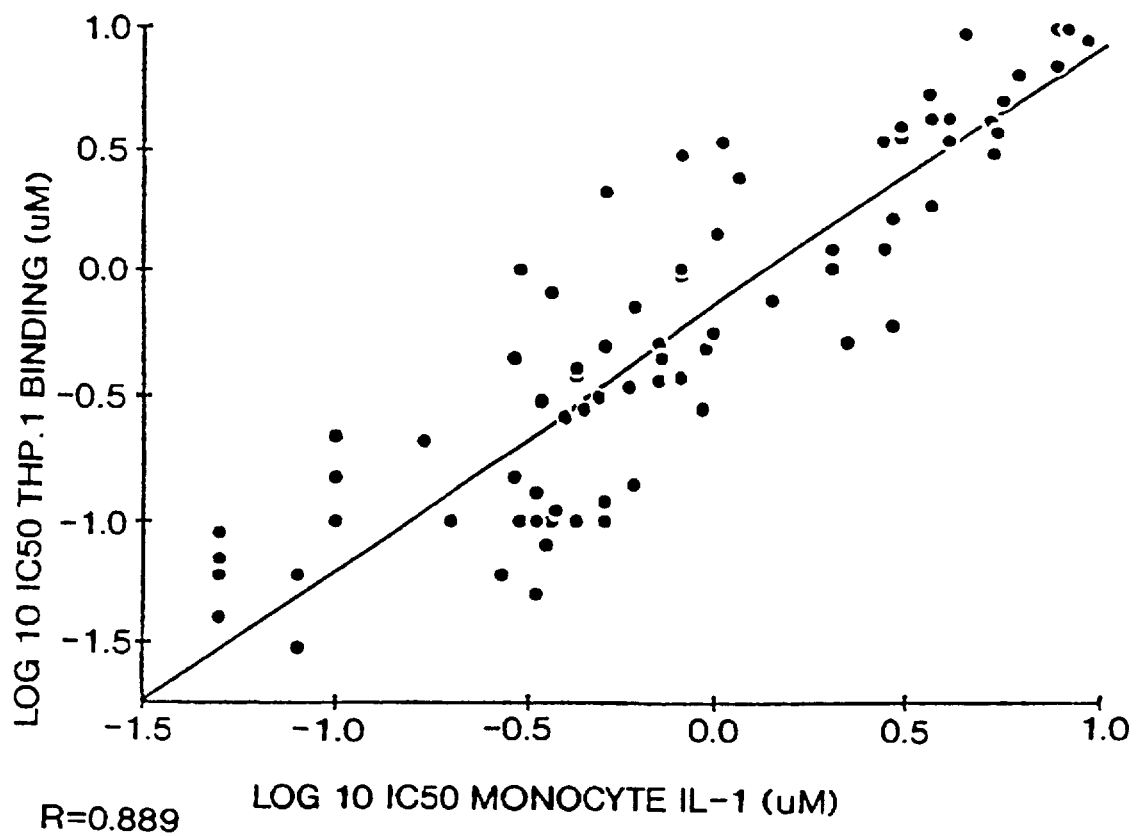
FIG. 5 illustrates the specificity of the CSAID binding activity. A large number of the pyridinyl imidazole compounds spanning three different structural classes with known $IC_{50}$s for cytokine synthesis inhibition were tested in a competitive binding assay in which radiolabeled Compound I was used. There was a high degree of correlation between the two activities (R=0.889) suggesting that the binding event is a necessary step in the inhibition of cytokine production.
Figure 6:
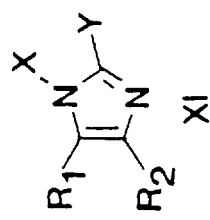
FIG. 6 illustrates the regioselectivity of the CSAIDs. Four pairs of regioisomeric forms of the CSAIDs were tested in the bioassay and the competitive binding assay. Only one isomeric form of the respective pair was active with identical $IC_{50}$s in both assays.

A substantial number of pyridinyl imidazole CSAIDs were tested in the radiolabel competitive binding assay. The rank order potency and the IC50s of the compounds was highly correlative to that determined by the human monocyte bioassay (FIG. 5). Furthermore, the competitive binding activity was regioselective (FIG. 6). These results underline the particular usefulness of the binding assay to the cytokine suppressive effects of these compounds and is considered particularly advantageous for SAR development and providing the means to help eludicate the molecular target.

Binding is highly specific for the pyridinyl imidazole CSAIDs. A series of non-structurally related compounds of varied pharmacological activities were tested in the competitive binding assay. They include the specific cyclooxygenase inhibitors, 5-lipoxygenase inhibitors, dual CO/LO inhibitors, PDE IV inhibitors, immunosuppressive macrolides, steroids, and others (Table II). None of the compounds tested at 100 μM demonstrated competitive binding.

A list of non-pyridinyl imidazole CSAIDs, related anti-inflammatory or immunosuppressive compounds tested in the competitive CSAID binding assay is provided in Table II. Unless otherwise indicated, no competitive binding was observed up to 100 μM.

TABLE II

| Cyclooxygenase Inhibitors | Steroid |
|---|---|
| Indomethacin | Dexamethasone |
| Naproxen | |
| Selective 5-Lipoxygenase Inhibitors | Novel Anti-Inflammatories |
| Hydroxyurea class | IX270 |
| Aminophenol class | Tenidap (IC50 = 139 μM) |
| | Romazarit |

TABLE II-continued

| 5-Lipoxygenase Translocation Inhibitor | Peroxisome Proliferators |
|---|---|
| MK886 | Wyeth 14643 |
| | Clofibrate |
| Dual Inhibitors | AH Receptor Agonists |
| Phenidone | 3-Methylcholanthrene |
| NDGA (IC50 = 154 μM) | βNaphthoflavone |
| Immunosuppressives | Miscellaneous |
| FK506 | Tibenelast |
| Azaspirane | Tetrandrine |
| Rapamycin & Analogs | |
| PDE$_{IV}$ Inhibitor | |
| Rolipram | |

Figure 7:
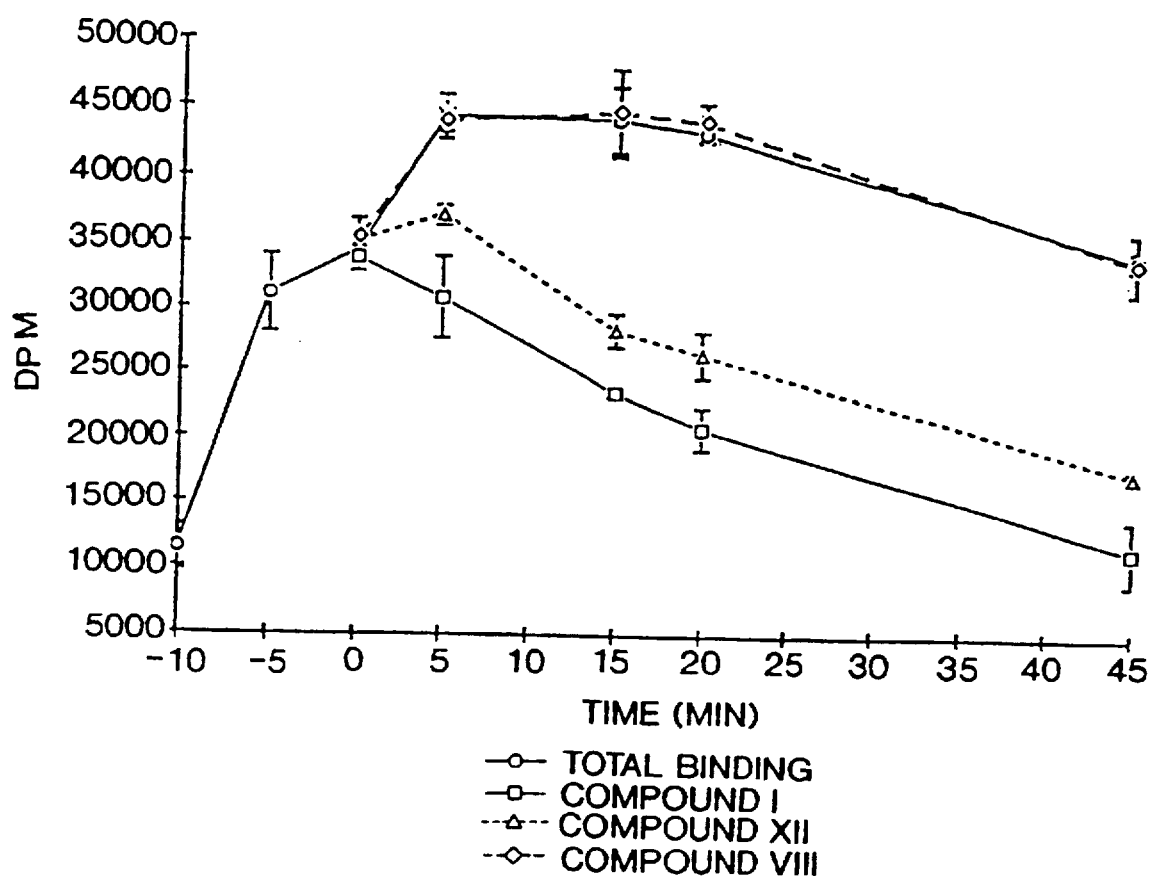
FIG. 7 illustrates that the binding of radiolabeled SB 202190 is saturable, specific and reversible. THP.1 cytosol was incubated with 50 nM radiolabeled SB Compound I for 15 minutes to allow saturable binding to equilibrate, at which time 30 μM of the cold ligand was added and at various intervals, specific binding was determined. The binding is reversible with Compound VII and to a lesser extent, Compound XI and not at all with Compound VIII, the $IC_{50}$s of these compounds in the bioassay were 20 nM, 50 nM and >5 μM respectively.
Figure 8A:
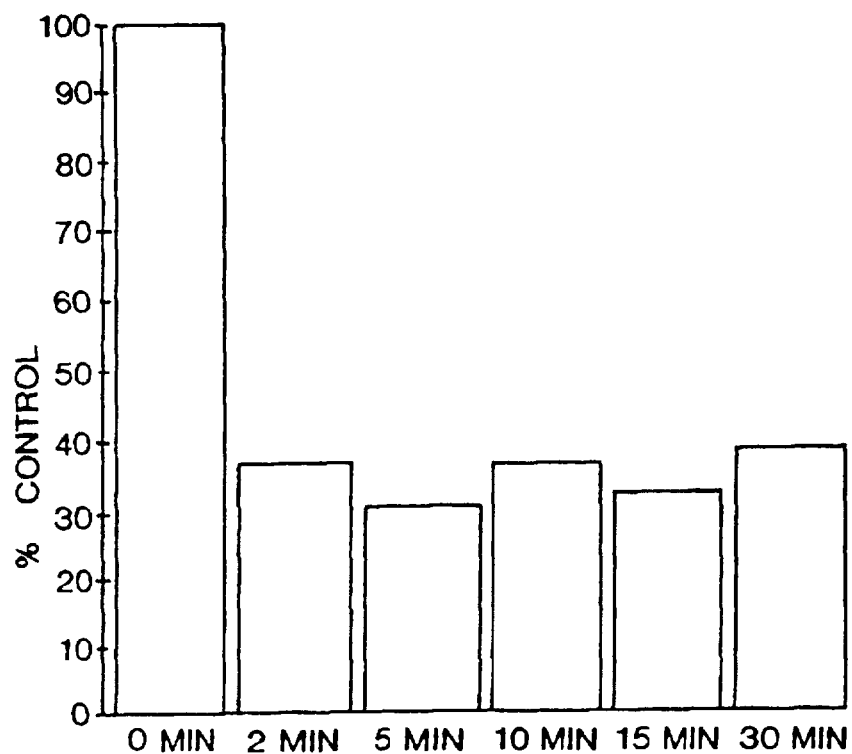
FIGS. 8A and 8B illustrate the CSAID binding activity is protease and heat sensitive. THP.1 cytosol was subjected to trypsin (100 μg/ml) (Panel A) and heat (56° C.)(Panel B) treatment. Maximum abrogation of binding activity was achieved within 2 minutes after treatment with trypsin. The binding activity was abrogated after incubation at 56° C., showed a gradual loss at 37° C. and was relatively stable at 22° C. and 4° C.
Figure 8B:
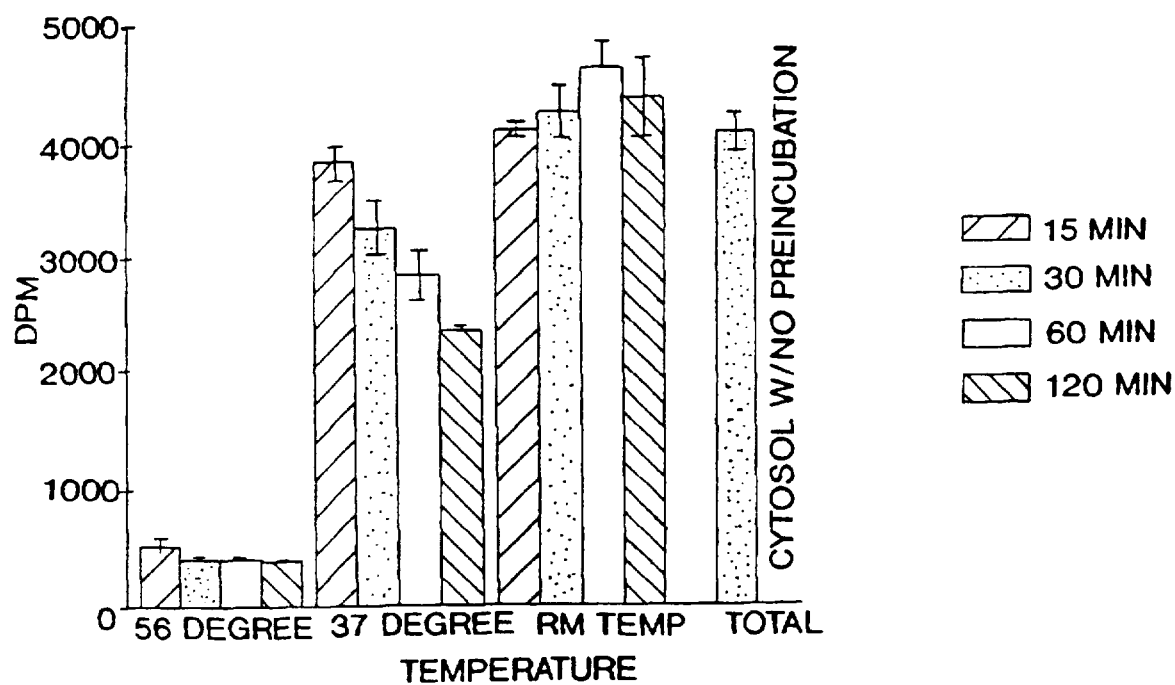

Having established a cell source and a binding assay further characterization of CSBP established that the CSAID binding is saturable, specific and reversible (FIG. 7), follows a rapid on and off rate, the binding activity is sensitive to protease and heat treatment (FIG. 8) and is protein concentration dependent (data not shown).

The CSAID binding activity in human monocytes is indistinguishable from that determined for THP.1 by the criteria established for the binding activity listed above.

The binding is pH dependent with an optimal pH range from 5 to 8 and is independent of divalent cations and is sensitive to high salt concentration which is reversible.

Purification of CSBP

The purification of the CSBP from THP.1 cells was accomplished as follows:

Materials

The following compounds were synthesized by the methods outlined in PCT application, US93/00674 and US93/00675 both filed Jan. 13, 1993.

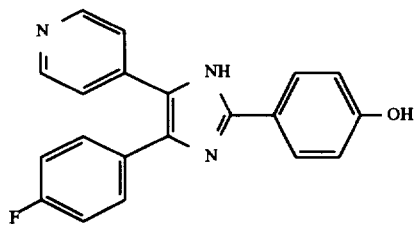

Compound I

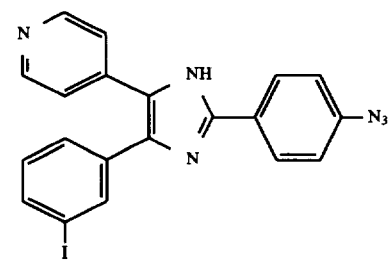

Compound V

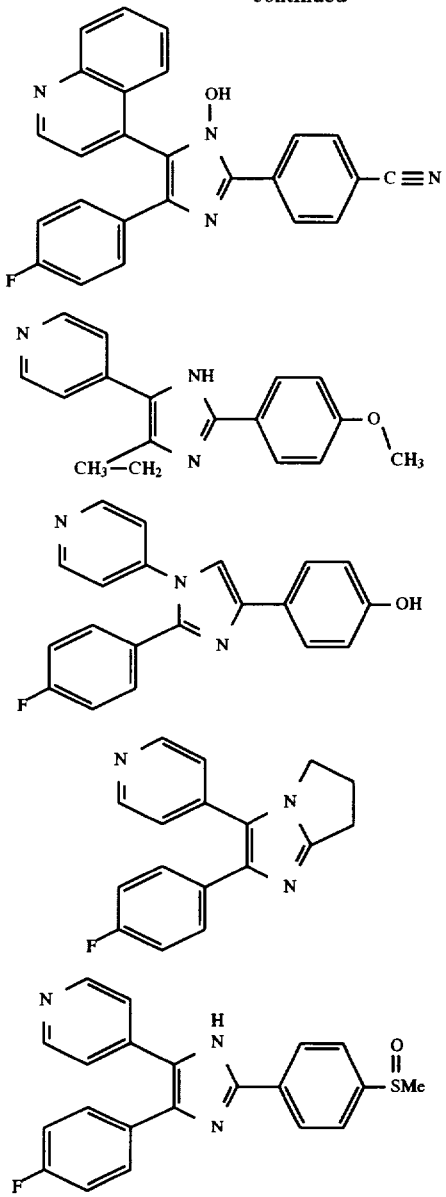

Compound VII

Compound VIII

Compound IX

Compound X

Compound XI

The radiolabeled compounds II and IV were prepared as described above. Polyclonal and monoclonal antibodies against actin (rabbit (cat #65-096) and mouse (cat. #69-100), respectively) were purchased from ICN Biomedicals. The peptide NH₂-Ile-Thr-Ala-Ala-Gln-Ala-Leu-Ala-His-Ala-Tyr-Phe-Ala-Gln-Tyr-Cys-COOH (Seq. I.D. No. 1) was synthesized by standard solid phase FMOC chemistry (see for example: Fields, G. B., et al. *Int'l. Peptide Protein Res.* 35: 161–214 (1990), purified and coupled to maleimide activated keyhole limpet hemocyanin (KLH) (Pierce Chemical Co. Cat #77105A) by conventional methods, and used to inoculate rabbits. All other chemicals were of reagent grade and unless otherwise specified, were not purchased from a particular vendor.

Growth of THP.1 Cells

THP.1 cells were grown and processed as follows:

THP.1 cells are grown in RPMI-1640 medium with 25 mM Hepes, 10% FBS (8% in reactors), 10 mM glutamine, and 0.05% pluronic F-68. The cells were passed on a ¾ days cycle with an average cell count of 2×10⁶ (seeding density between 2×10⁵ and 3×10⁵). A high density cell recycle in shake flasks was used to scale-up the cells to the large reactors. In this process, the total volume of the shake flask was spun down and resuspended with the same volume of fresh medium. Therefore, seeding density increased with each passage, giving a higher density of cells per volume. The densities ranged from 6×10⁶ to 12×10⁶.

From the shake flasks, two scale-up procedures were used to obtain the required volumes. Initially, two 80 L artisan reactors (60 L working volume) were used. Every five days, 50 L was taken out of both reactors and harvested. The cells were then fed with an additional 50 L until the total required volume was reached. Alternatively, cells were grown in a 30 L artisan and used to seed the 250 L Abec reactor (totaling working volume was 150 L). 120 L was harvested every five days and the 30 L left was refed. The seeding density was between 3×10⁵ and 5×10⁵. The pH for both types of reactors was controlled between 7.0 and 7.2. $CO_2$ was used as the controlling acid and sodium bicarbonate as the buffer. The D.O. was set at 30 percent for the Artisans reactors and 20 percent for the Abec reactor.

Preparation of THP.1 Cytosol

Cells were lysed by nitrogen cavitation in 20 mM TrisHCl pH 7.4, 1 mM $MgCl_2$, 1 mM PMSF, 1 µM pepstatin A and 1 µM leupeptin. Insoluble material was pelleted at 10,000×g for 10 min and the supernatant further clarified by a 100,000×g centrifugation for 1 h at 4° C. The supernatant from the final centrifugation was collected and is hereafter referred to as the THP.1 cytosol.

Measurement of CSAID Binding Activity

The same (typically 200 µg protein) was incubated with appropriately diluted ³H-Compound 1 (50 nM) at room temperature for 60 min to allow the binding to achieve equilibrium. Free ligand was separated from bound ligand on a 1.5 ml Sephadex G-10 column in 20 mM TrisHCl pH 7.4. The fraction encompassing the void volume was collected and the radioactivity was assessed by liquid scintillation counting. Protein concentrations were determined by the bicinchoninic acid assay (Pierce).

Superose 12 Chromatography

Approximately 100 to 250 ml of THP.1 cytosol was applied at 14.5 cm h⁻¹ to a 5 L Superose 12 column (Pharmacia; 11.5×50 cm) equilibrated in 10 mM $NaPO_4$ pH 7.0 and 150 mM NaCl at 4° C. Fractions were collected (50 ml) and assayed for CSAID binding activity; a single peak of activity corresponding to an elution volume for a protein of $M_r$~50,000 was pooled (200 to 500 ml).

Hydroxylapatite Chromatography

The material from the Superose 12 column were applied at 30 cm h⁻¹ to a 160 ml Hydroxylapatite HA column (Cal. Biochem; 5.0×8.0 cm) equilibrated in 10 mM $NaPO_4$ pH 7.0 at room temperature. The column was eluted with a 10 to 200 mM $NaPO_4$ gradient over 2.5 column volumes. Fractions (30 ml) were collected and assayed for CSAIDs binding activity. A protein peak containing approximately 60% of the CSAID binding activity applied to the column was pooled (50 to 250 ml).

Radiophotoaffinity Labeling of CSBP

The following protocol was used for about 30 ml of sample but can be adapted for larger or smaller volumes. The hydroxylapatite pool was concentrated to about 30 ml using an Amicon stir cell (YM30 membrane, 70 psi $N_2$). Insoluble material in the concentrate was removed by centrifugation (10,000×g for 30 min in SS34 rotor at 4° C.). The supernatant (450 mg protein) was used in the labeling reactions, which were performed in 6-well microtiter plates (Nunc). Six reactions were carried out using the following reagents and protocol. Approx. 60 mg. of protein (4 ml) was added to 0.25 ml buffer (10 mM $NaPO_4$ pH 7.0, 150 mM NaCl) and 0.25 ml 50 nM radioactive (i.e. "hot") $^{125}$I Compound IV (final concentration of 2.5 nM, 250 µCi) in dim light and allowed to stand on ice for 10 to 15 min. The microtiter plate was exposed to >300 nm light at a distance of 5 to 10 cm for 2 min while on ice. The reactions were chased with Compound IV (Compound VI being the "cold" (i.e. non-radioactive) form of Compound IV) as follows. A 1 mM stock of Compound VI was prepared by adding 0.3 ml 10 mM Compound VI to 2.7 ml 50% ethanol in 10 mM NaPO$_4$ pH 7.0 and 150 mM NaCl. Compound VI (0.5 ml 1 mM) was added to each labeling reaction in dim light and allowed to stand for 10 to 15 min on ice. The reactions were exposed to light as for the radioactive labeling. Unreacted Compounds IV and VI can be removed from labeled protein by the preparative isoelectric focusing or electrophoresis steps; or for samples of smaller volume, removed by gel filtration chromatography on Sephadex G-25 (1.6×12 cm) in 20 mM NaPO$_4$ pH 7.4 and 150 mM NaCl.

Analytical Electrophoresis, Autoradiography and Immunoblotting

Sodium dodecyl sulfate-polyacrylamide gel electrophoresis (SDS-PAGE) was performed under reducing conditions essentially as described by Smith B. J., *Meth. in Mol. Biol.*, Vol 1, pp. 44–57 (1984). Samples were run on 0.75 mm thickness 16 cm (4% stacking, 10 or 12% separating) or 10 cm (12% pre-cast, Jule) stab gels using the Hoefer SE 600 or Mighty Small electrophoresis systems, respectively. Protein was stained by either coomassie blue R350 (Pharmacia) or silver (Silver Stain Plus, BioRad). Molecular weight protein standards were purchased from Amersham or Bio-Rad. For blotting, proteins were transferred to a polyvinylidene difluoride membrane (Millipore) in 192 mM glycine/25 mM Tri pH 8.3 and 20% (v/v) methanol using a Genie electrophoretic blotter (Idea Scientific) at 15 V. Protein labeled with $^{125}$I was visualized by autoradiography using Hyperfilm-MP (Amersham) after overnight exposures at −70° C. The membrane was blocked with 5% gelatin in 20 mM TrisHCl pH 7.5 and 500 mM NaCl before incubation with the appropriate antiserum diluted 1,000 to 5,000-fold in buffer. The antibody complexes were detected with anti-mouse or anti-rabbit immunoglobulin G (Amersham) coupled to horse radish peroxidase and visualized by luminol phosphorescence on Hyperfilm-ECL (Amersham).

Preparative Isoelectric Focusing

Preparative isoelectric focusing was performed using a Rainin RF3 recycling free flow focusing protein fractionator at 4° C. overnight, concentrated to about 3 ml with an Amicon stir cell (YM30 membrane, 70 psi N$_2$), and brought to 10% glycerol and 1% ampholyte (Pharmacia Ampholine or Pharmalyte pH 4 to 6) for a final volume of about 10 ml. Before the sample was applied to the RF$_3$, a 1% ampholyte/10% glycerol solution was pre-focused for 1 to 1.5 h (until the voltage, current, power and temperature were at baseline). The sample was injected into bubble port 14 using a needle and syringe. The system was allowed to equilibrate as for the pre-focusing before collecting 3 ml fractions. Labeled CSBP was identified by monitoring the radioactivity, and the appropriate fractions pooled.

Preparative SDS-Page

Preparative SDS-PAGE was performed using the BioRad Model 491 Preparative cell. The pooled fractions from the preparative isoelectric focusing were concentrated to 2 to 3 ml with an Amicon stir cell (YM30 membrane, 70 psi N$_2$). Approximately 2 to 2.5 ml of the concentrate was brought to about 3 ml in 100 mM Tris pH 6.8, 2% SDS, 100 mM 2-mercaptoethanol, 10% glycerol and 0.01% bromophenyl blue before incubating at 100° C. for 3 to 5 min. The sample was applied to the gel (2 cm 4% stacking gel, 6 cm 11% separating gel) and run at 40 mA in 192 mM glycine/25 mM Tris pH 8.3 and 0.1% SDS at room temperature. Fractions (2.5 ml) were collected and assayed for radioactivity in order to identify where labeled CSBP eluted from the gel.

Results

Partial Purification of CSBP

A typical partial purification of CSBP from THP.1 cytosol is summarized in Table III. As indicated, the recovery of activity is 20% and the level of purification is 3-fold. This was characteristic of CSBP recovery and purification during evaluation of a number of chromatography resins (anion and cation exchange, hydrophobic interaction with (NH$_4$)$_2$SO$_4$, blue sepharose, heparin sepharose, etc.); the purification scheme as listed in the Table III gave the best recovery and most reproducible results. Since attempts to purify CSBP further while following CSAID binding activity resulted in poor recovery of activity, this was as far as the purification was taken before photoaffinity labeling.

TABLE III

Purification of CSBP from THP.1 cytosol

| Sample | Activity, dpm[a] | Protein, mg | Specific Activity, dpm mg$^{-1}$ |
|---|---|---|---|
| THP.1 cytosol[b] | 5.0 × 10$^8$ | 6800 | 7.4 × 10$^4$ |
| Superose 12 | 1.6 × 10$^8$ | 1200 | 1.3 × 10$^5$ |
| Hydroxylapatite | 9.6 × 10$^7$ | 500 | 1.9 × 10$^5$ |

[a]activity is expressed as the $^3$H radioactivity (disintegration per minute, dpm collected in the CSAID binding assayed as described above and corrected for the total sample.
[b]THP.1 cytosol was prepared from starting material equivalent to approximately 10$^{11}$ cells.

Photoaffinity Labeling of CSBP

Figure 9:
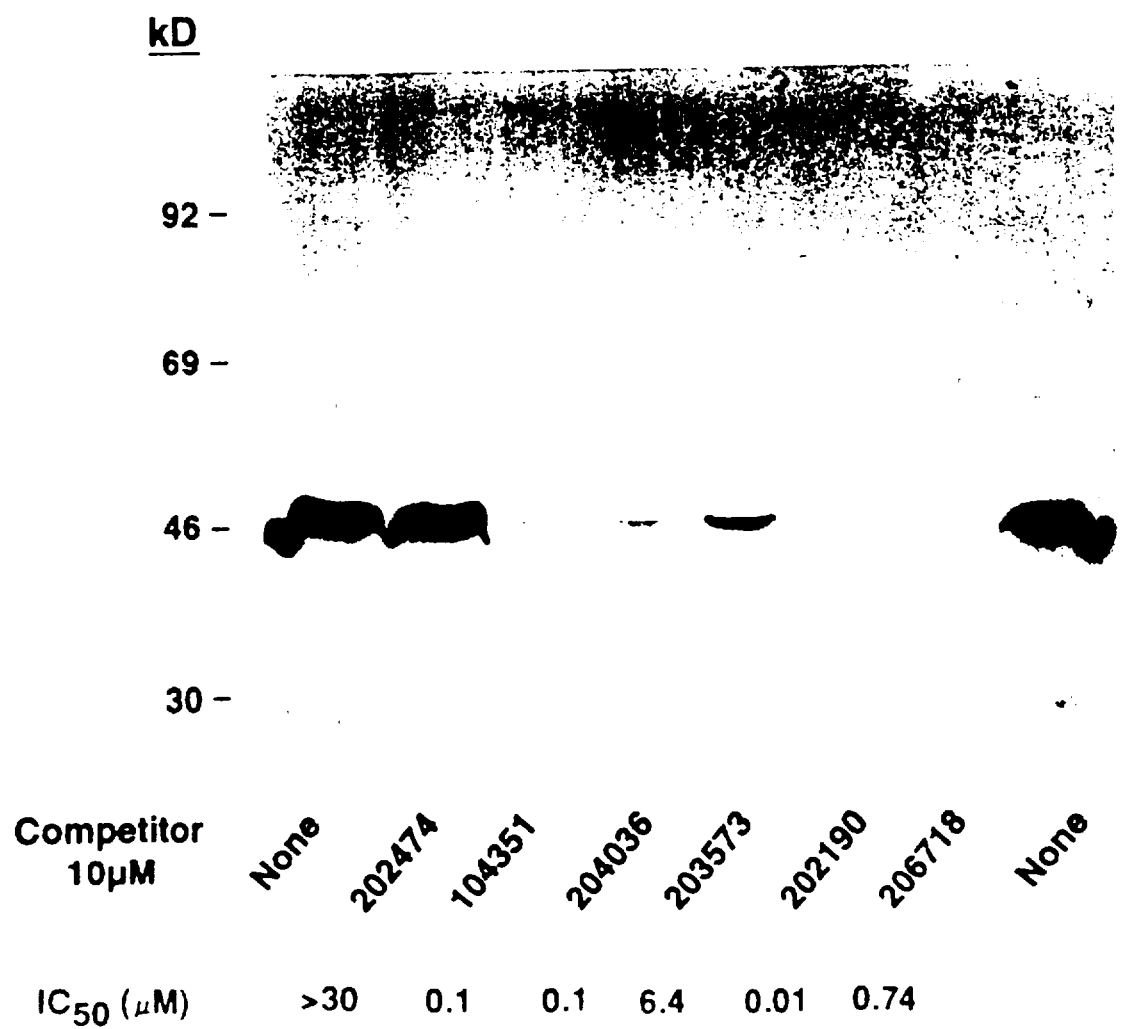
FIG. 9 illustrates the analysis of photoaffinity labeling of CSBP by SDS-PAGE and Autoradiography. Approximately 40 μg of protein was pre-incubated with the inhibitors listed above the gel at 10 μM before photoaffinity labeling with $^{125}$I Compound IV (2.5 nM). The reactions were analyzed by SDS-PAGE and autoradiography as described herein.

CSBP was covalently labeled with the $^{125}$I, aryl azide CSAID derivative Compound IV. The reaction was very specific as illustrated in FIG. 9, which shows that a single protein of M$_r$ 43,000 was labeled (the lanes labeled "None"). During the partial purification described above the CSAID binding activity eluted as a single peak from the Superose 12 gel filtration chromatography with a molecular weight corresponding to a protein of M$_r$ 45,000 to 50,000. Collectively these two analyses indicate the CSBP is a single-chain, or "monomeric" protein of M$_r$ 43,000.

FIG. 9 also illustrates the specificity of the labeling. In the middle lanes of the gel, protein was preincubated with a non-radioactive CSAID (10 µM) before the photoaffinity labeling with $^{125}$I Compound IV (2.5 nM). The extent to which each CSAID competed with the photoaffinity label correlates well with its potency in a cellular assay. That is the more potent the compound is in its ability to suppress IL-1 production in human monocytes, the more effectively it prevented photoaffinity labeling of the CSBP. Thus, CSBP is the protein labeled with Compound IV.

Purification of Labeled CSBP

Figure 10:
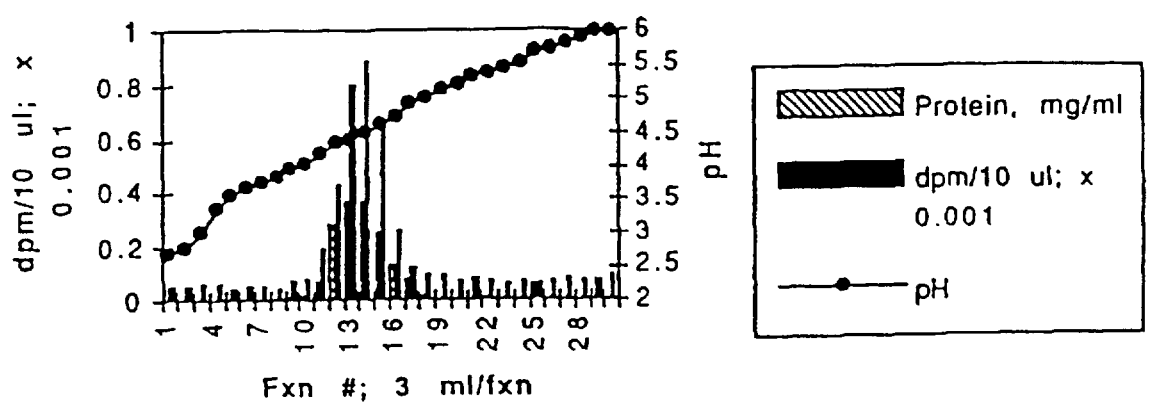
FIG. 10 illustrates that analysis of fractions from preparative isoelectric focusing. Protein labeled with $^{125}$I Compound IV was applied to the Rainin RF3 and analyzed as described herein.

In order to identify CSBP by its amino acid sequence, the labeled protein was further purified from the partially purified CSBP used for photaffinity labeling. The strategy to accomplish this was preparative isoelectric focusing, preparative SDS-PAGE and reversed-phase HPLC. The results of the preparative isoelectric focusing are shown in FIG. 10. The isoelectric point of the labeled protein corresponded to a pH of about 4.5. Western analysis indicated that some, but not all, of the actin was removed by this procedure. In addition, almost 70% of the protein applied eluted with the labeled protein (50% recovery of radioactivity). This was also demonstrated by SDS-PAGE and silver staining analysis (data not shown). Thus, for this application preparative isoelectric focusing did not provide a substantial purification of the desired protein.

Figure 11A:
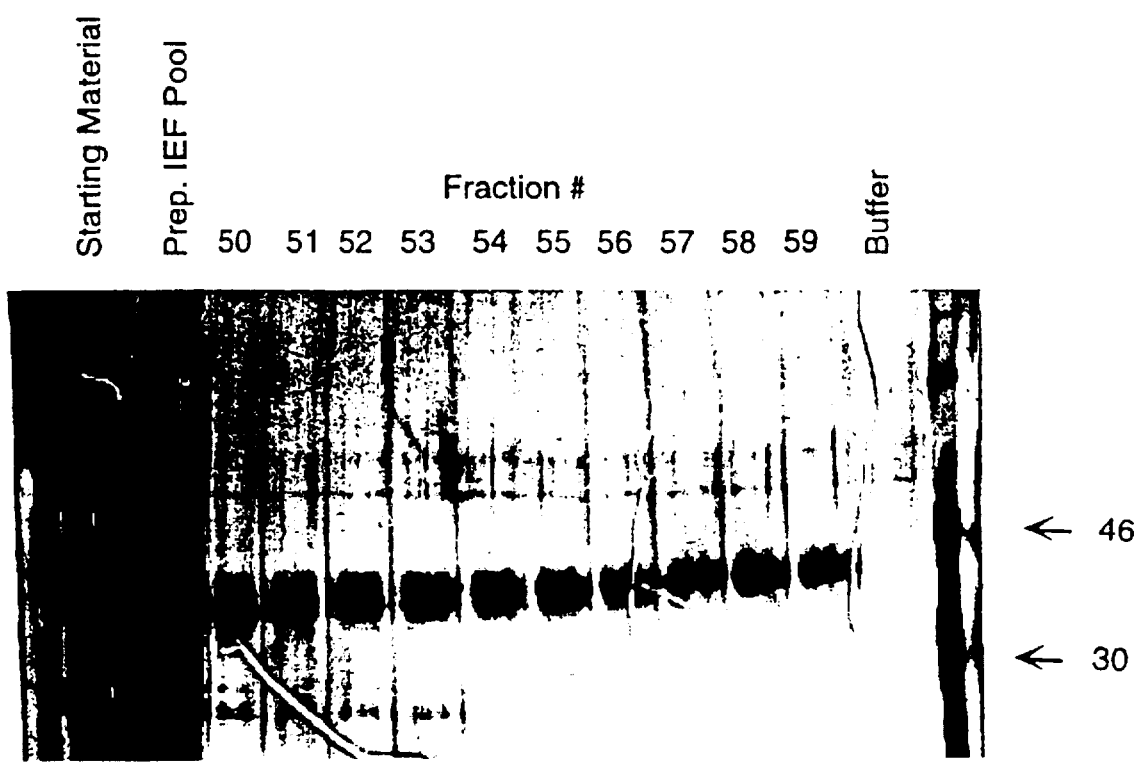
FIGS. 11A and 11B illustrate the analysis of preparative SDS-PAGE fractions by (A) SDS-PAGE and Silver Staining, and (B) Radioactivity. Fractions were analyzed as described hereinbelow.
Figure 11B:
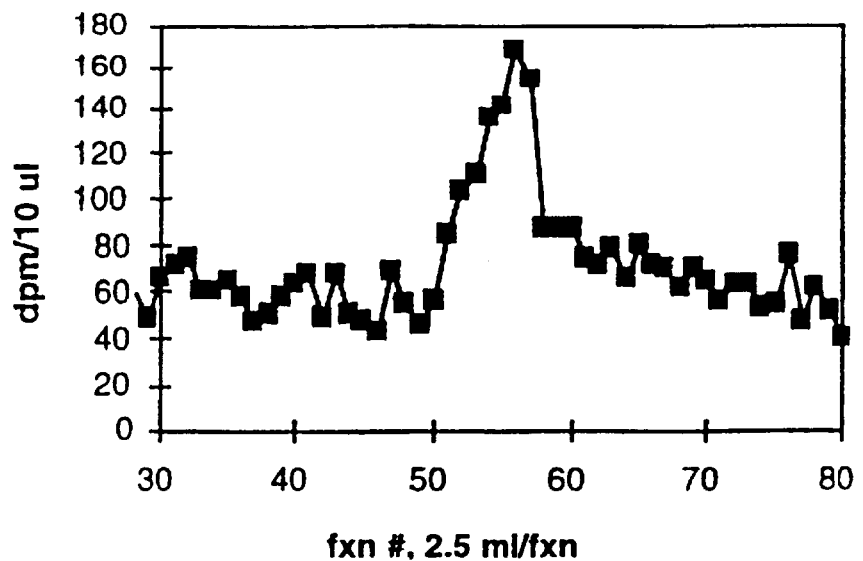

The most substantial purification of labeled CSBP was obtained by preparative SDS-PAGE. The material pooled from preparative isoelectric focusing was applied to a gel using the BioRad Model 491 Preparative Cell. As illustrated in FIG. 11, the radioactive fraction corresponding to a protein of about 43 kDa (fraction 56) has at least 90% of the non-radioactive protein removed by this procedure. In addition, unincorporated label is also removed.

Characterization of CSBP

Figure 12:
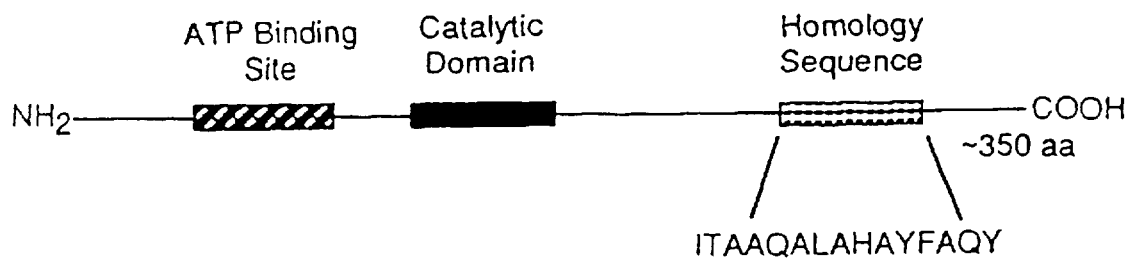
FIG. 12 illustrates the homology of unique amino acid sequence discovered during analysis of CSBP to MAP kinase. The peptide sequence (SEQ ID NO:1) is listed below the linear representation of MAP kinase of the 15 residues: 9 identical (60%), 13 identical or homologous (87%).

After preparative SDS-PAGE, labeled CSBP was applied to reversed-phase HPLC, where a protein peak coeluting with the radioactivity was collected. Comparison of the protein concentration (determined by amino acid analysis) to the specific radioactivity of the sample demonstrated that only 10% of this protein was labeled (assuming a protein $M_r$ of 43,000). N-terminal sequence analysis identified actin sequences corresponding to 30 to 40 amino acids downstream from the expected amino terminus. Internal sequence analysis following fragmentation with trypsin or CNBr generated approximately 90% actin sequences, but about 10% of the peptides gave unique sequences. One of the sequences from the tryptic digest had strong (85%) homology, but was not identical, to a C-terminal sequence found in a family of Ser/Thr protein kinases known as the mitogen-activated (MAP) kinases (FIG. 12; See also: Ray, L. B. & Sturgill, T. W., *Proc. Nat'l. Acad. Sci. (USA)*, 85:3753-3757 (1988)).

A peptide based on the sequence with homology to the MAP kinases was synthesized and used to inoculate rabbits for the production of antisera. Western analysis and autoradiography of labeled THP.1 cytosol 2-D gels demonstrated that 1) antibodies against actin or MAP kinases did recognize proteins on the blot, but not the radiolabeled protein; 2) the antibody prepared from the tryptic peptide recognized the radiolabeled protein. Thus, CSBP appears to have homology to, but is distinct from, the MAP kinases. Given the role of kinases in regulating translation (Pelech and Sanghera, *Science* 257:1355-66 (1992)) and the effect of CSAIDs on IL-1 and TNF translation, a kinase is not inconsistent as the molecular target for CSAIDs.

Isolation and Characterization of the CSBP gene:

This invention provides an isolated nucleic acid molecule encoding the human CSBP. Two amino-terminal peptide sequences were obtained from the protein fraction comigrating with the radioactive photoaffinity probe. One of these was derived from a trypsin digest of the radioactive protein fraction but was not itself radioactive, and had the sequence:

ILE THR ALA ALA GLN ALA LEU ALA HIS ALA TYR PHE ALA GLN TYR (Seq. I.D. No. 1)

The second was obtained from an 8 KDa cyanogen bromide fragment associated with radioactivity and had the sequence: XXX (GLN) LEU LEU ASN ASN LE (VAL/PHE) LYS (PHE) GLN LYS LEU THR (Seq. I.D. No. 2)

where ( ) represents an uncertain assignment and / represents an uncertainty between two amino acids. XXX is an unknown amino acid. A search of Genbank indicated that peptide sequence I.D. No. 1 was homologous to the MAP kinase family of protein kinases, whereas peptide sequence I.D. No. 2 was unique. Based on these two sequences, two degenerate oligonucleotide DNA probes were synthesized using the genetic code to reverse translate the protein sequences, and tables of mammalian cell codon preferences (Grantham, R. et al., *Nucl. Acid Res.* 9: (1981)).

1. GCYCAYGCTAYTTYGCYCARTA (Seq. I.D. No. 3) and
2. AAYAAYATYKTBAARTTYCAAA (Seq. I.D. No. 4)

where
Y=C or T
R=A or G
K=G or T
B=G, C or T

Hence the two mixed oligonucleotides consist of 128 and 384 unique sequences respectively. A cDNA library made from human monocytes treated with GM-CSF (Livi, G. P. et al., *Mol. Cell Biol.* 10: 2678-86 (1990) in the commercial vector λZAP (Stratagene) which was screened at low stringency by hybridization to a 50:50 combination of the two synthetic oligonucleotide mixtures labeled with γ-32 P ATP. Labeling of the oligonuleotides followed published methods (Current Protocols in Molecular Biology), typically labeling 3 μg of mixed oligonucleotide with 250 μCi γ-$^{32}$ P ATP and using all of this in a 250 μl hybridization volume. The manufacturer's recommended conditions for plating and lifting phage were followed (see Stratagene λZAP protocol, Stratagene, La Jolla, Calif.) using the BB4 host strain. One additional step was to prewash the filterlifts at 65° C. in 2×SSPE/0.1% SDS twice for 30 min. prior to prehybridization to remove bacterial debris.

Subsequently, prehybridization and hybridization with the labeled oligonucleotide probes were performed at 37° C. for 24–72 h in 6×SSPE, 5×Denhardt's solution, 0.1% SDS and 100 μg/ml phenol/chloroform extracted yeast tRNA. (20× SSPE is 3M NaCl, 0.2M NaH$_2$PO$_4$, 0.02M EDTA pH7.4.50×Denhardt's solution is 10 g polyvinylpyrrolidone (MW 40,000), 10 g Bovine serum albumin and 10 g Ficoll 400 per liter H$_2$O.

After hybridization the filters were washed twice under each of the following conditions.

1. 6×SSPE, 0.1% SDS, room temp, 10–15 min.
2. 6×SSPE, 0.1% SDS, 37° C., 10–15 min.
3. 3M tetramethylammonium chloride solution (500 g Me$_4$NCl, 1.38 liter H$_2$O, 73 ml 1M tris pH 8.0, 5.8 ml 0.5M EDTA, 7.3 ml; 20% SDS filtered through 0.45 μM filter), 37° C., 30 min (see: *Proc. Nat'l. Acad. Sci. USA* 82: 1585–1588 (1985) for a description of this technique).

Filters were exposed to Kodak film for 3–5 days in the presence of intensifying screens, and overlapping positives in duplicate filters picked and cycled through the same procedure until pure plaques obtained.

Phage was excised with M13 helper phage R408 in the recA⁻ *E. coli* host XL-1 blue according to manufacturers procedures (Stratagene).

After two subsequent rounds of replating and hybridization of positively hybridizing plaques using just the oligonuclcotide mixture #1, a single homogeneous phage was obtained which hybridized in a Southern blot with the oligonucleotide #1 (Seq. I.D. No. 3) but not with oligonucleotide #2 (Seq. I.D. No. 4). Sequencing of the DNA insert of this phage revealed an open reading frame at one end which encoded part of the No. 2 unique peptide sequence. I.D. No. 2 above. The amino sequence so encoded was:

Asn Ile Val Lys Cys Gln Lys Leu Thr. (Seq. I.D. No. 5).

The rest of the open reading frame (FIG. (13) Seq. I.D. No. 6 and 7 was homologous to several protein kinases including the cdc2 and the MAP kinase families. Based on this homology, it is predicted to be missing approximately 130 amino acids from the amino terminus which is obtained via a second round of library screening with the amino terminal region of the obtained cDNA clone. The other end of the cDNA contains the poly A sequence corresponding to the 3' terminus of the mRNA from which it was obtained (FIG. 14, Seq. I.D. No. 8).

Accordingly, based on initial cDNA (FIG. 13), oligonucleotides (5'-CCTCGGAGAATTTGGTAGATAAGG-3' (Seq. I.D. No. 9) and 5'-AACATTGTGAAATG-TCAGAAGCTTACAGATGACCAT-3' (Seq. I.D. No. 10)) were designed from the 5' end of the sense strand, and used to screen for cDNAs encoding the amino terminus of CSBP. The oligonucleotides were labelled at their 5' ends with polynucleotide kinase and $\gamma$-$^{32}$P-ATP. $10^6$ plaques from a GM-CSF stimulated human monocyte library constructed in $\lambda$ZAP were screened on duplicate nitrocellulose filters which had been prewashed prior to hybridization in 2×SSPE, 0.1% SDS at 50° C. After blocking for 48 h with 50% formamide, 6×SSPE, 5×Denhardt's and 100 μg/ml sheared, denatured salmon sperm DNA, filters were hybridized in the same buffer with the above labelled oligonucleotides for 24 hours at 42° C. The filters were then washed twice with 2×SSPE, 0.1% SDS at room temperature, followed by two washes in 1×SSPE, 0.1% SDS at 42° C. and two washes in 0.5×SSPE, 0.1% SDS at 42° C. before detection of hybridizing plaques by autoradiography. Positive plaques which appeared on duplicate filters were picked and replated and the procedure repeated twice until unique plaques could be isolated and phagemid DNA released according to manufacturer's protocol (Stratagene Cloning Systems, LaJolla, Calif.). The cDNAs were sequenced on an Applied Biosystems automated DNA sequencer (ABI 373A) using universal and specific oligonucleotide primers and Taq polymerase cycle sequencing, and the sequences merged and examined using Lasergene software on a Macintosh IIci. Both strands were completely sequenced at least once in each cDNA clone.

Description of cDNAs.

Figure 15:
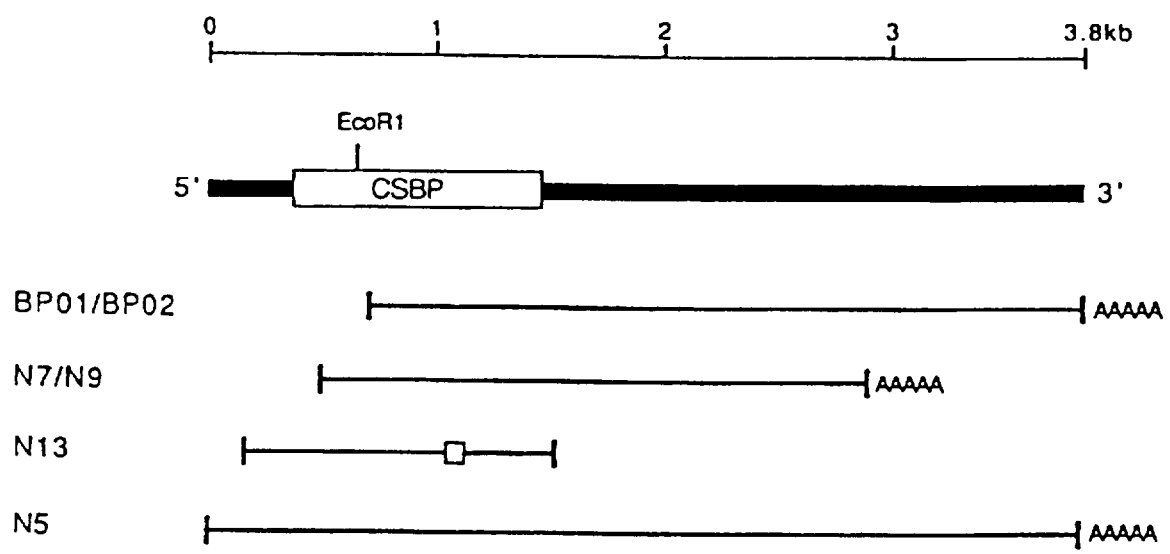
FIG. 15 illustrates diagramatically the various CSBP cDNAs described herein.

A summary of the cDNAs isolated is illustrated schematically in FIG. 15. There are four different cDNAs which have been completely sequenced and are identical in regions of overlap, with one exception to be described below. BP01/02 is the cDNA first isolated above, the partial sequence of which is given in FIGS. 13 and 14. The longest cDNA is 3.8 kb long (N5) Seq. I.D. No. 11 and Seq. ID NO: 12 contains 370 nucleotides of 5' untranslated sequence, a 1.1 kb coding region and 2.4 kb of 3' untranslated sequence. The extreme 3' end is terminated by a poly A stretch characteristic of mRNA, and is preceded by the expected consensus sequence for polyadenylation. The N7 cDNA has a 3' untranslated region of only 1.4 kb terminating in a site and poly A run suggesting an alternative polyadenylation site. On a Northern blot a probe derived from the coding region hybridizes to an ca. 4.2 kb mRNA suggesting that the longest cDNA isolated is close to full length.

The coding translates into a protein of 360 amino acids with calculated molecular weight of 41.5 kDA, matching the size of the protein identified by photoaffinity crosslinking with $^{125}$I-labelled Compound IV (FIG. 16). The predicted isoelectric point (ca. 5.6) is also close to that observed (Ca. 5.0). Examination of the sequence indicates that it contains both the tryptic peptide sequence ITAAQ... (boxed) (SEQ ID NO:1) and the cyanogen bromide sequence xxx LNNIVK... (boxed) (SEQ ID NO:2) obtained by sequencing of the CSAIDs binding protein in THP.1 cells. These sequences are preceded by the appropriate cleavage sites (arrows). The predicted size of the cynaogen bromide fragment (8 kDa) matches the size of the fragment which remains associated with the $^{125}$I-labelled radiophotoaffinity label [Compound IV] after cyanogen bromide treatment of the CSAIDs binding protein.

The N13 cDNA (FIG. 15) Seq. I.D. No. 13 and Seq. ID No: 14 is identical to the other three cDNAs with the exception of a 75 nucleotide region starting at position 1054 of the N5 cDNA. This difference results in a protein of identical size with amino acids 230–255 altered. (FIG. 17). The two different sequences are 43% identical at the nucleotide level, and 44% identical at the amino acid level. Without wishing to be bound by any particular theory, it is likely that the two variants result from alternative internal exon splicing, although allelic variation cannot be excluded. For ease of description, two proteins are referred to herein as CSBP1 (corresponding to the N5 cDNA) and CSBP2 (corresponding to the N13 cDNA).

Figure 18:
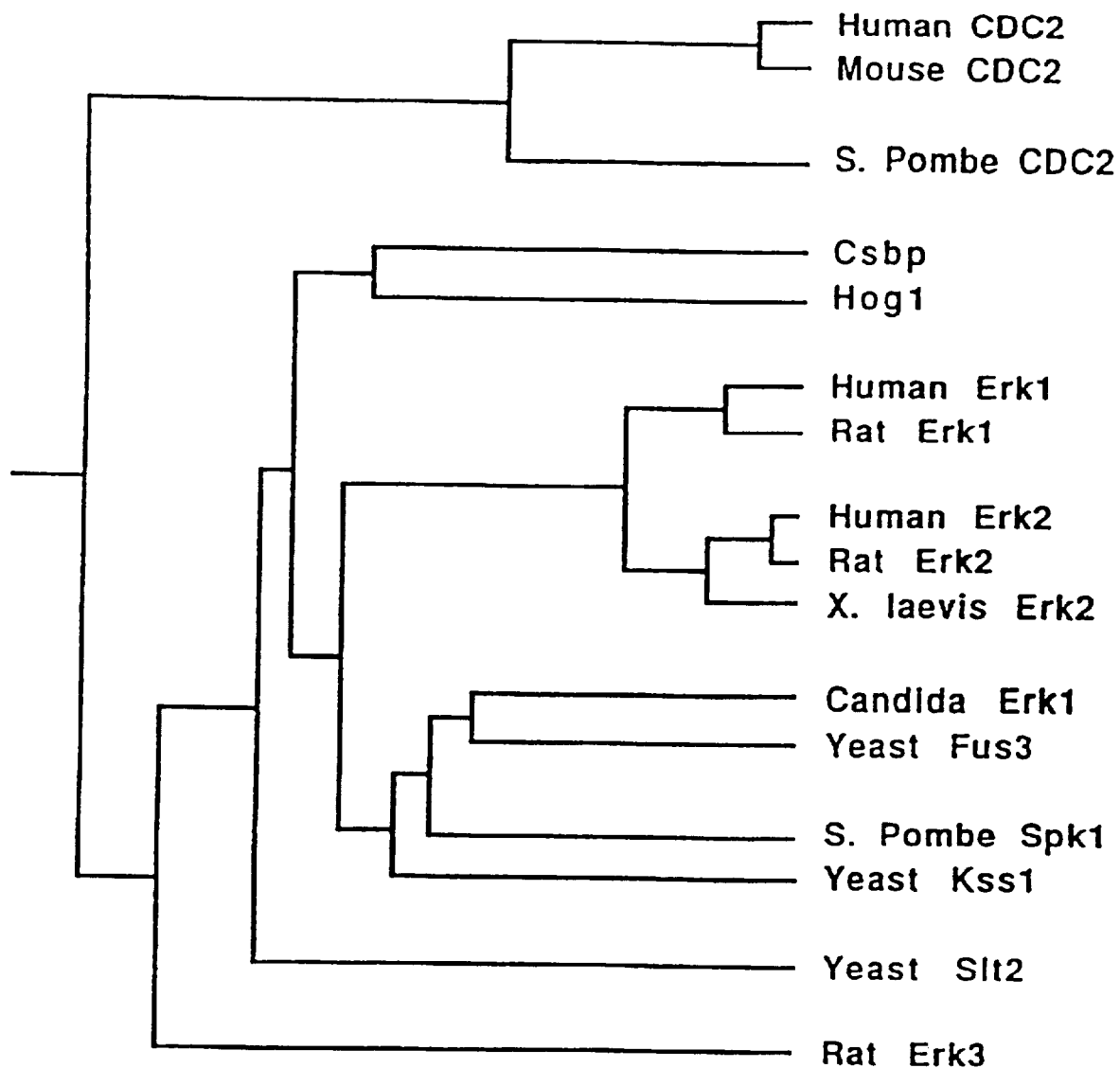
FIG. 18 illustrates a phylogenetic tree of various protein kinases.

Comparison of the CSBP sequence to proteins in the GenBank/EMBL or Swissprot databases indicated close homology to a family of proteins known as MAP (Mitogen Activated Protein) or erk (extracellular regulated) kinases (Boulton, et al., "Erks; A Family of Protein Serine-Threonine Kinases that are Activated and Tyrosine Phosphorylated in Response to Insulin and NGF", Cell, 65: 663–675 (1993). This family of protein kinases is conserved from yeast to man as indicated in the phylogenetic tree in FIG. 18 with the closest published homologue being the yeast HOG1 gene (Brewster et al., Science 259: 1760–63 (1993). An alignment of the CSBPs with selected members of this family (FIG. 19) shows a conservation of all 11 protein kinase motifs (I through XI), including residues identical in all protein kinases (bold) (Hanks et al., Science, 241: 42–52 (1988). Two boxed motifs in regions VI and VII indicate that the kinases phosphorylate serines and threonines (Hanks et al., 1988). Hence the CSBPs are protein kinases.

A threonine and tyrosine in a T×Y sequence (asterisks, proximal to domain VIII are known to be regulatory phosphorylation sites for Erk 1 and Erk 2 (Payne, et al., EMBO J., 10: 885–892, 1991). These two residues are phosphorylated by MEK (MAPK or ERK Kinase) in response to various extracellular signals, resulting in an activation of the serine/threonine kinase activity of the MAP kinases (Kosako, et al., EMBO. J., 12: 787–794 (1993). The conservation of these amino acids in the CSBPs suggests tha they are also regulated by a MEK in response to extracellula stimuli such as LPS. These findings suggest that the CSBP: lie within a cascade of protein phosphorylation events which communicate cell surface stimuli to events such as translational regulation, within the cell. Much of the behavior of the CSBP in suitably stimulated cells can be predicted based o analogy with the known properties and behavior of the MAJ kinases (Marshall, et al., Curr. Opin. Genetics & Develop. 4: 82–89 (1994).

A multiple tissue Northern blot with a coding region cDNA probe suggests expression of CSBP mRNA in mos tissues. A Southern blot at high stringency (0.1% SSPE 0.1% SDS) suggested a single gene; however lower strin gency washes may reveal closely related kinases. Gen mapping experiments using a panel of human/mouse hybrid cell lines available commercially indicated that the gene fo CSBP resides on human chromosome 6.

Expression in E. coli

Figure 20:
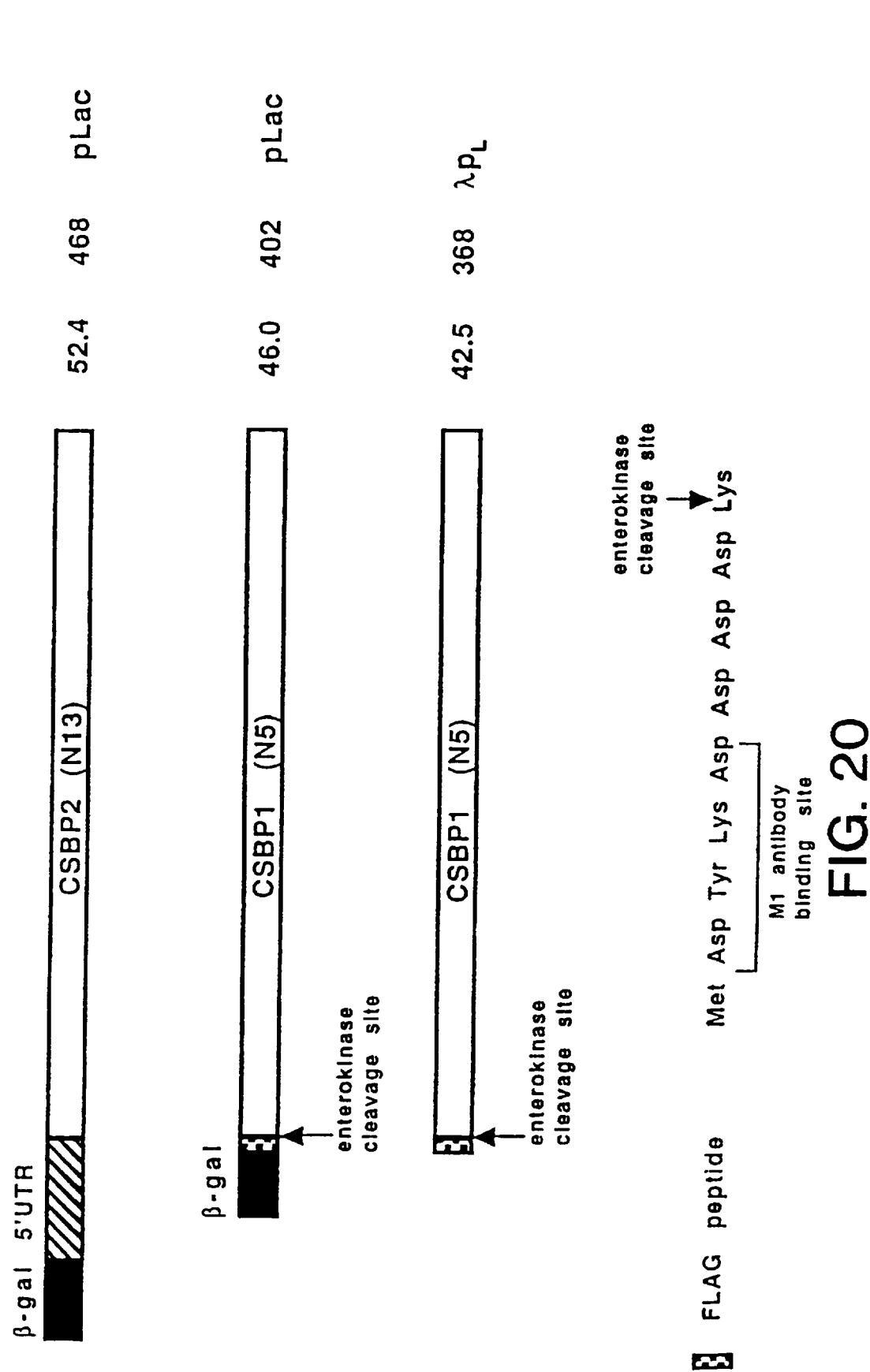
FIG. 20 illustrates the results of expression of CSBP (SEQ ID NOS:12 or 14) in E. coli.

To confirm that the proteins encoded by the isolate cDNAs can bind to CSAIDs, the cDNAs were expressed i E. coli and yeast. In E. coli the CSBPs were expressed a fusion proteins with β-galactosidase and/or an enterokinas cleavable FLAG epitope tag (FIG. 20) (FLAG is a commer cial epitope for which reagents are available through IBI Kodak). In the latter case this was achieved by the design o a synthetic oligonucleotide linker with an initiation site antibody recognition sequence, and enterokinase cleavag site. Proteins were expressed under the control of either th pLac (e.g., Bluescript KS vector from Stratagene, LaJolla, Calif.) or λpL (Shatzman, et al., *N.Y. Acad. Sci.*, 478: 233–248 (1986)) promoters and the radiophotoaffinity probe [Compound IV] shown to specifically crosslink proteins of the expected sizes in cell lysates. Lysates also contain Compound IA specific binding activity. One can conclude that both CSBP1 and CSBP2 are the molecular targets of the CSAIDs within cells.

Protein expressed in *E. coli* was purified by passage over an affinity matrix containing a monoclonal antibody to the FLAG epitope according to manufacturer's instructions.

Expression in Yeast

An alternative system for expression of CSBP is *Saccharomyces cerevisiae*, not only for purification but also to assess function. The yeast HOG1 (High Osmolarity Glycerol response) gene, (Brewster et al., supra) encodes a MAP kinase which is a close homologue of CSBP. Mutant hog1D strains show reduced growth on high-osmolarity medium and functional complementation of this phenotype with CSBP was tested.

CSBP2 was engineered for yeast expression as follows. A XhoI site was introduced at the initiation codon of CSBP2 by the polymerase chain reaction (Mullis, and Faloona, *Method in Enzymd.*, 155: 335–50 (1987) using the following oligonucleotide primers: 5'-cgccctcgagatgtctcaggagaggcccacg-3' Seq. I.D. No. 15 and 3'-ctaagacctaaaacctgaccg-5', Seq. No. 16. The 525-bp PCR fragment was digested with XhoI and BglII and subcloned into the same sites in p138NBU, a modification of p138NB (McHale et al., *Mol. Pharm.* 39: 109–113 (1991) in which the TRP1 selectable marker was replaced with URA 3. The resulting plasmid was then digested with BglII and SalI and ligated with a BglII XhoII fragment containing the 3' end of CSBP2. The final construct contains partial 2 micron sequences for maintenance at high copy number, with CSBP2 mRNA expression driven by the copper-inducible CUP1 promoter and terminated by the yeast CYC1 transcriptional terminator. Plasmid p138NBU-CSBPN13B was found encode the wild-type CSBP2 protein. Transformations of parent (YPH499 MATa ura3-52 lys2-801$^{am}$ ade2-101 trp1-D63 his3D200 leu2-D1) and hog1D (JBY10 [YPH499+hog1::TRP1]) strains (Brewster, et al., *J. Bacteriol.* 153: 163–168 (1983) Ura$^+$ prototrophs were isolated and grown to $^A$540 of 1.0 in synthetic complete medium lacking uracil (Hicks et al., *Genetics* 83: 245 (1976). CSBP2 expression was induced by the addition of 150 mM CuSO$_4$. Cells were harvested at 5 hr, resuspended 20 mM Tris-HCl pH7, 1 mM MgCl$_2$, 1 mM phenylmethylsulfonylfluoride and disrupted by vortexing in the presence of 0.45 mm glass beads. Extracts were centrifuged at 1,500×g for 5 min at 4°.

Radiophotoaffinity probe (Compound IV) was shown to specifically crosslink a protein of the expected size in lysates of both p138NBU-CSBPN13A and p138NBU-CSBPN13B, which was not present in wild type or hog1D strains containing control plasmid (p138NBU) and grown under similar conditions. Lysates also contained $^3$H Compound Ia specific binding activity. Therefore both CSB1 (SEQ ID NO:12) and CSB2 (SEQ ID NO:14) bind CSAIDS.

The proteins of this invention are preferably made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g., yeast or mammalian) cells by methods well known in the art (Ausubel et al., supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ(*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, YCp19 (Saccharomyces). See, generally, "DNA Cloning": Vols. I & II, Glover et al., eds. IRL Press Oxford (1985) (1987) and; T. Maniatis et al. "Molecular Cloning", Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. Alternatively, gene fusions may be created whereby the gene encoding the binding protein of interest is fused to a gene encoding a product with other desirable properties. For example, a fusion partner could provide known assayable activity (e.g. enzymatic) which could be used as an alternative means of selecting the binding protein. The fusion partner could be a structural element, such as a cell surface element such that the binding protein (a normally cytosolic component) could be displayed on the cell surface in the form of a fusion protein. It may also be desirable to produce mutants or analogs of the protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis and the formation of fusion proteins, are well known to those skilled in the art. See, e.g.. T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1(*Mol. Cell Biol.* 7:4125–29) which uses the CMV promoter to drive expression. Both these latter two vectors can be employed for transient or stable (e.g. using G418 or hygromycin resistance) expression in mammalian cells. Insect cell expression systems, e.g., Drosophila, are also useful, see for example, PCT applications US 89/05155 and US 91/06838 as well as EP application 88/304093.3 and Baculovirus expression systems.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired binding protein.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The binding proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with a binding protein of the present invention, or its fragment, or a mutated binding protein. Serum from the immunized animal is collected and treated according to known procedures. When serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the protein of interest, or fragment thereof, can be screened for various properties; i.e., for isotype, epitope, affinity, etc. Alternatively, genes encoding the monoclonals of interest may be isolated from the hybridomas by PCR techniques known in the art and cloned and expressed in the appropriate vectors. Monoclonal antibodies are useful in purification, using immunoaffinity techniques, of the individual proteins against which they are directed. The antibodies of this invention, whether polyclonal or monoclonal have additional utility in that they may be employed reagents in immunoassays. RIA, ELISA, and the like. In addition they can be used to isolate the CSBP from human cells and determine the effect of different stimuli and compounds on the phosphorylation state and protein kinase activity of endogenous CSBP. The antibodies could be used to establish a tissue culture based assay for discovery or modification of novel compounds which block the phosphorylation or kinase activity of CSBP. An example of such an assay would be to incubate human monocytes or monocytic cell lines with a compound or compound mixture prior to treatment with LPS for a defined time period, followed by immunoprecipitation of CSBP with antibody and assessmen of its phosphorylation state via immunoblot or chromatography or measurement of its kinase activity with appropriate protein or peptide substrate.

This invention provides a method for determining whether a ligand previously not known to bind to a CSBP can bind to such a protein. The method comprises contacting the ligand to be identified with cytosolic fraction from THP.1 cells and measuring its ability to compete with a known radioactive CSAID, as described above, in a CSAIDs binding assay. Alternative methods include contacting the ligand to be identified with a whole-cell expressing the coding sequence of a CSBP under conditions sufficient for binding of ligands previously identified as binding to such a receptor In other embodiments cell membrane fractions comprising the CSBP fusions or isolated CSBP free or immobilized on solid supports may be used to measure binding of the ligand to be tested. When recombinant cells are used for purpose of expression of the CSBP it is preferred to use cells with little or no endogenous CSBP activity so that binding if any is due to the presence of the expressed protein of interest. A mentioned previously, a specifically designed indicator o receptor binding can be constructed. For example a fusion protein can be made by fusing the CSBP of this invention with a protein domain which is sensitive to CSBP/ligand binding. Such a domain referred to here as an indicato domain is capable, itself, or in association with accessory molecules, of generating an analytically detectable signa which is indicative of receptor ligand binding. A variation o this approach is to express CSBP as a fusion protein (e.g. fused to FLAG peptide) in THP.1 or other mammalian cell: and to use the fusion peptide as a means of isolating th recombinant CSBP after suitable stimulation and pretreatment of THP.1 cells. Such expression can be achieved with numerous mammalian expression vectors which utilize viral promoters. eg CMV, RSV and polyadenylation sequences, et. SV40. bovine growth hormone, and a selectable marker such as G418 or hygromycin for selection of stable transfectants.

Cytosolic preparations from transfected or transformed cells expressing such fusions may be employed. All of the above techniques that are useful for ligand identification are also useful in drug screening and drug development protocols.

Alternatively, the purified recombinant protein could be used to substitute for crude THP.1 cell lysates in a competitive binding assay with Compound Ia. This assay is useful to screen for novel compound which bind CSBP, or as a way to assess alterations to compound which is known to bind. The availability of purified protein allows alternative configurations of the assay from those described previously for the crude material. For example, if the protein is covalently linked to a tag, such a protein binding site for configuration in a colorimetic assay, e.g., conjugated antibody, or to an enzyme for direct detection of enzyme activity, e.g., horseradish peroxidase or alkaline phosphatase. binding to novel compounds displayed on a solid matrix could be detected. Such compounds could include low molecular weight organic molecules, peptides, peptoids, and proteins. In the latter case, the protein can be used as a way to isolate other proteins in its signaling cascade, for example, those that are in the pathway for activation of cytokine translation in activated monocytes. The protein may also be used to isolate naturally occurring regulatory molecules within mammalian cells that act by a CSAIDs binding mechanism. Finally, the protein can be used to identify target peptides displayed on the surface of phage.

The knowledge that the CSBPs encode protein kinases suggest that recombinant forms can be used to establish a protein kinase activity. Typically this would involve the direct incubation of CSBP with a protein or peptide substrate in the presence of $\gamma$-$^{32}$P-ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While the specific substrates are not yet known, candidates include CSBP itself (autophosphorylation) and peptides related to known MAP kinase substrates. Other substances might be discovered by incubating CSBP with random peptides conjugated to solid supports or displayed by phage (see above) or by incubation of CSBP with mammalian cell lysates (e.g. THP.1 cell lysates) and $\gamma$-$^{32}$P-ATP, followed by separation of the labelled target proteins, and sequencing. Kinase activity may also be detected by use of antiphosphotyrosine antibodies. The protein kinase activity of CSBP may require incubation with a specific MEK. This may be achieved by preincubating CSBP with lysates from stimulated eukaryotic cells (e.g., LPS treated THP.1 cells) and ATP. Alternatively, it may be possible to isolate a more active form of CSBP from HOG1 deletion strains of yeast expressing the human CSBP and grown in high osmolarity conditions.

These assays permit the discovery and modification of compounds which inhibit CSBP kinase activity in vitro. Such compounds would be expected to block cytokine synthesis in a comparable fashion to the compounds described herein. They could also lead to the discovery of novel substrates which themselves may be viable targets for discovery of novel compounds which block cytokine production.

It is expected that CSBPs, like other MAP kinases, will be activated by a MEK, hence the recombinant protein would allow the establishment of a second assay which measures the ability of CSBP to be phosphorylated by putative MEKs. In this case fractions from stimulated cell lysates (eg THP.1 cells stimulated with LPS) are incubated with CSBP in the presence of $\gamma$-$^{32}$P-ATP, and the incorporation of $^{32}$P-label into CSBP measured by separation and counting. Separation can be achieved in a number of ways: one way is to use a CSBP fused to an peptide or protein and separate via affinity chromatography or immunoprecipitation with the peptide or protein directed antibody. Alternatively the CSBP can be directly conjugated to beads or bound through a fusion peptide or protein (e.g., FLAG (peptide), glutathionine-S-transferase) and separated by centrifugation after incubation with cell lysates. Also tyrosine phosphorylation of CSBP could be detected by immunoprecipitation or immunoblot with commercially available anti-phosphotyrosine antibodies.

These assays can be used to discover compounds which block the activation of CSBP protein kinase activity and to improve the potency of already discovered compounds. These compounds would be expected to have utility due to their blocking of cytokine synthesis. The assays are also useful to discover novel MEKs which themselves may become targets for novel compounds which would block cytokine synthesis.

The ability of human CSBP to rescue a HOG1 deletion strain upon growth in conditions of high osmolarity allows for the direct screening of compounds which block CSBP activity in vivo. For example, compounds could be screened for their ability to block growth of a CSBP+/HOG1– yeast strain in high osmolarity but which have no effect on growth of the same strain in standard osmolarity or on a CSBP–/HOG1+ in high osmolarity. The sensitivity of the yeast based assay can be increased by introducing host mutations that affect the cell membrane and permeability (Gaber, et al., *Mol. Cell. Biol.* 9: 3447–3456. (1989).

In a compound screening embodiment of this invention, the CSBP in isolated, immobilized or cell bound form is contacted with a plurality of candidate molecules and those candidates are selected which bind to and interact with the protein. The binding or interaction can be measured directly by using radioactively labeled candidate of interest or indirectly by measuring an effect resulting from the interaction or binding of the candidate compound. Alternatively, the candidate compounds can be subjected to a competition screening assays, in which a known ligand, preferably labeled with an analytically detectable reagent, most notably radioactivity, is introduced with the compounds to be tested and the compound's capacity to inhibit or enhance the binding of the labeled ligand is measured. Compounds are screened for their increased affinity and selectivity for the CSBP.

To illustrate this aspect of the invention a natural product screen was performed.

The standard assay in which bound ligand is separated from free by exclusion chromatography using mini-columns was used to initiate a screening effort. Approximately 625 marine extracts, 202 microbial extracts and 233 extracts of plant material were tested for inhibition of $^3$H-Compound I binding to THP.1 cytosol. Two extracts were confirmed as antagonists of this binding, with $IC_{50}$'s of around 200 and 80 µg/ml respectively. This low hit-rate (0.2%) coupled with the failure to observe inhibition by any of a selected group of "nuisance extracts" indicates that the assay is sufficiently selective and robust to support a screening effort. While the potency of these two hits is rather weak, they were nevertheless accepted as leads for isolation of their active principle so that the primary assay could be evaluated as well as identification of the bioactive compounds.

The two extracts were subsequently fractionated and characterized.

Further refinement of the binding assay to facilitate high throughout screening can be achieved by the minor modification of separating bound ligand from free ligand using spin columns.

The discovery that the CSBPs of this invention are homologous to the MAP kinase family of serine-threonine protein kinases provides a specific rational for the treatment of a wide variety of acute and chronic inflammatory diseases. Accordingly, it is a further aspect of this invention to treat patients suffering from the effects of cytokine-mediated inflammatory disease with a CSBP inhibitory amount of a CSAID. Illustrative examples of such diseases include, without limitation, diseases associated with the central nervous system such as senile dementia of the Alzheimer's type(SDAT), mutiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft verus host disease. Thus this invention contemplates the treatment and/or amelioration of such disease by administering a CSBP inhibiting amount of a compound. Without wishing to be bound by any particular theory of the functioning of the CSBPs of this invention, it is believed that among the useful inhibitors of CSBP function are those compounds which inhibit the kinase activity of the CSBPs. Other sites of inhibition are, of course, possible owing to its position in a signal transduction cascade. Therefore, inhibiting the interaction of CSBP with one or more of its upstream or downstream substrates is also contemplated by this invention.

This invention also contemplates pharmaceutical compositions comprising compounds when identified by the above methods and a pharmaceutically acceptable carrier. Pharmaceutical compositions of proteinaceous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified drug is non-proteinaceous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 10 milligrams per day and higher although it may be administered in several different dosage units. Tablets containing from 0.5 to 10 mg. of active agent are particularly useful.

Depending on the patient condition, the pharmaceutica composition of the invention can be administered for prophylactic and/or therapeutic treatments. In therapeutic application, compositions are administered to a patien already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutica compositions can be carried out with dose levels and patter being selected by the treating physician. In any event, the pharmaceutical composition of the invention should provide a quantity of the compounds of the invention sufficient to effectively treat the patient.

The nucleic acid embodiment of this invention is particularly useful in providing probes capable of specific hybridization with human CSBP sequences. Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. This invention contemplates, for example using receptor encoding probes in the diagnostic evaluation of disease states characterized by an abnormal, i.e. increased or decreased level of receptor gene expression. Alternatively, the probes can be used to identify individuals carrying chromosomal or molecular mutations in the gene encoding the receptor. Depending on the conditions employed by the ordinary skilled artisan, the probes can be used to identify and recover additional examples of this receptor (in its genomic or cDNA form) from other cell types and individuals. As a general rule the more stringent the hybridization conditions the more closely related genes will be that are recovered.

Also within the scope of this invention are antisense oligonucleotides predicated upon the sequences disclosed herein for the CSBP. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to mRNA and inducing degradation by endogenous nucleases such as RNase I or by inhibiting the translation of mRNA by inhibiting its binding to regulatory factors or ribosomal components necessary for productive protein synthesis. Additionally the antisense sequences can be use as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures which are incorporated herein by reference for purposes of background (Cohen, J. S., *Trends in Pharm. Sci.* 10:435 (1989) and Weintraub, H. M. *Scientific American* January (1990) at page 40).

This invention also contemplates the use of the DNA sequences disclosed herein in gene therapy. Because CSBP is a protein kinase it is possible to make a site specific mutant which is inactive as a kinase but will block activation of the endogenous CSBP when coexpressed in the same cell, i.e., it is a dominant negative mutant (Kolch et al., *Nature* 349: 426–428 (1991). The DNA encoding this mutant protein could be used in gene therapy to reduce chronic inflammation. There are many vector and delivery systems available to direct DNA into target cells in vivo, e.g. adenovirus, retroviruses.

This invention also contemplates antibodies, monoclonal or polyclonal directed to epitopes corresponding to amino acid sequences disclosed herein from the CSBP. Particularly important regions of the receptor for immunological purposes are those regions associated with ligand binding domains of the protein. Antibodies directed to the regions are particularly useful in diagnostic and therapeutic applications because of their effect upon protein-ligand interaction. Methods for the production of polyclonal and monoclonal antibodies are well known, see for example Chap. 11 of Ausubel et al. (supra).

This invention also provides pharmaceutical compositions comprising an effective amount of antibody or fragment thereof directed against the CSBP to block binding of the naturally occurring ligands to that protein in order to treat or ameliorate disease states associated with protein activation.

Transgenic, non-human, animals may be obtained by transfecting appropriate fertilized eggs or embryos of a host with nucleic acids encoding the CSBP disclosed herein, see for example U.S. Pat. Nos. 4,736,866; 5,175,385; 5,175,384 and 5,175,386. The resultant transgenic animal may be used as a model for the study of CSBP/ligand interaction. Particularly, useful transgenic animals are those which display a detectable phenotype associated with the expression of the protein. Drugs may then be screened for their ability to reverse or exacerbate the relevant phenotype. This invention also contemplates operatively linking the CSBP coding gene to regulatory elements which are differentially responsive to various temperature or metabolic conditions, thereby effectively turning on or off the phenotypic expression in response to those conditions.

The nucleic acid probes disclosed herein can be used to clone the cognate version of the human CSBP gene from a desired experimental animal species; for example the murine version. Strains of mice can be developed in which said gene has been eliminated by conventional gene knock-out technology. The gene can then be substituted/or replaced by the human CSBP DNA of this invention to yield a mouse for screening candidate drugs in vivo. Similar gene knockout and human protein inhibition studies can also be performed with yeast.

The purified protein of this invention is also useful in a reagent for structural studies with and without bound drug candidates as a means for the rational design of novel drugs affecting CSBP. For example, the recombinant protein may be used to derive the structure of the protein alone or complexed with Compound Ia and related compounds through X-ray crustallography, NMR or modelling from published structures of related protein kinases, e.g., CSK. A structure fosters an understanding of how the inhibitory compounds bind, and can lead to the design or discovery of further compounds which can block CSBP activity and hence be inhibitors of cytokine synthesis. There are now several examples of such structure-based design for other protein targets, e.g., HIV protease. Given the similarity of CSBP to several other kinases (e.g. the MAP and CDC kinases), such structural information will be useful in designing novel compounds which inhibit other members of the kinase family.

Both the nucleic acid encoding the CSBP and the CSBP itself are also useful as diagnostic reagents. The nucleic acid can be fashioned into probes (See: DNA Probes, 2 ed. Keller, G. H. and M. M. Manak, Stockton Press, 1993) and eployed to measure CSBP RNA levels in target samples, whereas the CSBP can be integated as a component of a diagnostic test to detect phosphorylated and/or unphosphorylated forms of the protein, thereby indicating the relative state of activation of the protein.

We claim:

1. An oligonucleotide capable of screening for cDNAs encoding a region of Cytokine Suppressive Anti-Inflammatory Drug binding proteins, the olignoucleotide comprising SEQ ID NO: 9 or NO: 10.

* * * * *

UNITED STATES PATENT AND TRADEMARK OFFICE
CERTIFICATE OF CORRECTION

PATENT NO. : 5,777,097
DATED : July 7, 1998
INVENTOR(S) : Lee et al.

It is certified that error appears in the above-identified patent and that said Letters Patent is hereby corrected as shown below:

In the title, please delete "comprising" and insert therefor --consisting of--.

In the Claims:
In Claim 1, line 3, please delete "comprising" and insert therefor --consisting of--.

Signed and Sealed this

Twenty-third Day of February, 1999

Attest:

Q. TODD DICKINSON

*Attesting Officer*      *Acting Commissioner of Patents and Trademarks*